US009427499B2

(12) United States Patent
Vepari et al.

(10) Patent No.: US 9,427,499 B2
(45) Date of Patent: Aug. 30, 2016

(54) SURFACE MODIFICATION OF SILK FIBROIN MATRICES WITH POLY(ETHYLENE GLYCOL) USEFUL AS ANTI-ADHESION BARRIERS AND ANTI-THROMBOTIC MATERIALS

(75) Inventors: Charu P. Vepari, Burlington, MA (US); David L. Kaplan, Concord, MA (US)

(73) Assignee: Trustees of Tufts College, Medford, MA (US)

(*) Notice: Subject to any disclaimer, the term of this patent is extended or adjusted under 35 U.S.C. 154(b) by 682 days.

(21) Appl. No.: 13/129,738

(22) PCT Filed: Nov. 17, 2009

(86) PCT No.: PCT/US2009/064673
§ 371 (c)(1),
(2), (4) Date: Dec. 8, 2011

(87) PCT Pub. No.: WO2010/057142
PCT Pub. Date: May 20, 2010

(65) Prior Publication Data
US 2012/0076771 A1    Mar. 29, 2012

Related U.S. Application Data

(60) Provisional application No. 61/115,248, filed on Nov. 17, 2008.

(51) Int. Cl.
| A61L 27/14 | (2006.01) |
| A61L 27/28 | (2006.01) |
| A61L 27/22 | (2006.01) |
| A61L 31/10 | (2006.01) |
| A61L 33/06 | (2006.01) |
| A61L 31/00 | (2006.01) |

(52) U.S. Cl.
CPC .............. *A61L 31/005* (2013.01); *A61L 31/10* (2013.01); *A61L 33/068* (2013.01)

(58) Field of Classification Search
CPC ... A61K 2300/00; C08L 89/00; A61L 27/26; A61L 27/227; A61L 27/14; A61L 31/10; A61L 33/068
See application file for complete search history.

(56) References Cited

U.S. PATENT DOCUMENTS

| 5,245,012 | A | 9/1993 | Lombari et al. |
| 6,902,932 | B2 | 6/2005 | Altman et al. |
| 8,501,172 | B2 | 8/2013 | Kaplan et al. |
| 9,040,073 | B2 | 5/2015 | Boison et al. |
| 9,068,282 | B2 | 6/2015 | Cannizzaro et al. |
| 2004/0199241 | A1 | 10/2004 | Gravett et al. |
| 2005/0260706 | A1 | 11/2005 | Kaplan et al. |
| 2006/0273279 | A1 | 12/2006 | Kaplan et al. |
| 2007/0187862 | A1 | 8/2007 | Kaplan et al. |
| 2010/0068740 | A1 | 3/2010 | Kaplan et al. |
| 2011/0046686 | A1 | 2/2011 | Kaplan et al. |
| 2011/0076384 | A1 | 3/2011 | Cannizzaro et al. |
| 2011/0135697 | A1 | 6/2011 | Omenetto et al. |
| 2011/0152214 | A1 | 6/2011 | Boison et al. |
| 2011/0171239 | A1 | 7/2011 | Kaplan et al. |
| 2012/0121820 | A1 | 5/2012 | Kaplan et al. |
| 2012/0123519 | A1 | 5/2012 | Lovett et al. |
| 2012/0171770 | A1 | 7/2012 | Numata et al. |
| 2014/0134240 | A1 | 5/2014 | Kaplan et al. |

FOREIGN PATENT DOCUMENTS

| JP | H05-43600 A | 2/1993 |
| JP | 2001-118544 A | 4/2001 |
| JP | 2008-295697 A | 12/2008 |
| WO | WO-97/08315 A1 | 3/1997 |
| WO | WO-03/056297 A2 | 7/2003 |
| WO | WO-04/000915 A2 | 12/2003 |
| WO | WO-2005/012606 A2 | 2/2005 |
| WO | WO-2008/118133 A2 | 10/2008 |
| WO | WO-2008/127401 A2 | 10/2008 |
| WO | WO-2008/127405 A2 | 10/2008 |
| WO | WO-2009/023615 A1 | 2/2009 |
| WO | WO-2009/061823 A1 | 5/2009 |
| WO | WO-2009/100280 A2 | 8/2009 |
| WO | WO-2009/126689 A2 | 10/2009 |
| WO | WO-2009/140588 A1 | 11/2009 |
| WO | WO-2009/155397 A2 | 12/2009 |
| WO | WO-2011/006133 A2 | 1/2011 |

OTHER PUBLICATIONS

Gotoh, Y., et al. 1997 Polymer 38(2): 487-490.*
Tziampazis, E., et al. 2000 Biomaterials 21: 511-520.*

(Continued)

*Primary Examiner* — Marsha Tsay
(74) *Attorney, Agent, or Firm* — Choate, Hall & Stewart LLP

(57) ABSTRACT

The present invention provides compositions and methods for the production of silk fibroin matrices surface-PEGylated on one or more surfaces. Such surface-PEGylated silk fibroin matrices can be used in biomedical applications, such as anti-adhesive and anti-thrombosis materials. Silk matrices may be surface-PEGylated, for example, by a reaction with a functional group-activated PEG. Controlling the degree of PEGylation on surface of silk fibroin matrix can regulate both the degradation rate of the silk matrix, and the differentiated adhesion of cells or differentiated adsorption of proteins on the surface of the silk matrix. The present invention also provides for silk fibroin matrices having one or more surfaces possessing differentiated adhesion properties, which allows for tissue integration on the adherent side and inhibition of tissue adhesion to the opposing tissues or organs. Embedding active agents in silk fibroin matrices provides more benefits, such as promoting tissue ingrowth on the adherent side of the matrix.

28 Claims, 9 Drawing Sheets

(56) References Cited

OTHER PUBLICATIONS

Vepari, C., et al. 2007 Prog Polym Sci 32: 991-1007.*
Gotoh, et al., "Chemical Modification of Silk Fibroin with Cyanuric Chloride-Activated Poly(ethylene glycol): Analyses of Reaction Site by 1H-NMR Spectroscopy and Conformation of the Conjugates", Bioconjugate Chemistry, vol. 4, No. 6, pp. 554-559, 1993.
International Preliminary Report on Patentability for PCT/US2009/064673, 8 pages (May 17, 2011).
International Search Report for PCT/US2009/064673, 5 pages (Sep. 29, 2010).
Written Opinion for PCT/US2009/064673, 7 pages (Sep. 29, 2010).
Gotoh, Y. et al., Synthesis of poly(ethylene glycol)-silk fibroin conjugates and surface interaction between L-929 cells and the conjugates, Biomaterials, 18(3): 267-271 (1997).
Altman, G. et al., Silk-based biomaterials, Biomaterials, 24(3):401-416 (2003).
Arai, T. et al., Biodegradation of *Bombyx mori* Silk Fibroin Fibers and Films, Journal of Applied Polymer Science, 91:2383-2390 (2004).
Arai, T. et al., Chemical Modification of *Bombyx mori* Silk Using Isocyanates, Journal of Applied Polymer Science, 79:1756-1763 (2001).
Bianco, P. et al., Bone marrow stromal stem cells: nature, biology, and potential applications, Stem Cells, 19(3):180-192 (2001).
Boada, J. et al., Determination of polyethylene glycol activated with cyanuric chloride in liposomes, Analytical Biochemistry, 253(1):33-36 (1997).
Campbell, P. et al., Engineered spatial patterns of FGF-2 immobilized on fibrin direct cell organization, Biomaterials, 26(33):6762-6770 (2005).
Cao, X. and Shoichet, M., Defining the concentration gradient of nerve growth factor for guided neurite outgrowth, Neuroscience, 103(3):831-840 (2001).
Chan, C.M. and Ko, T.M. al., Polymer surface modification by plasmas and photons, Surface Science Reports, 24:1-54 (1996).
Chen, J. et al., Human bone marrow stromal cell and ligament fibroblast responses on RGD-modified silk fibers, Journal of Biomedical Materials Research Part A, 67(2):559-570 (2003).
Cunniff, P. et al., Mechanical and Thermal Properties of Dragline Silk from the Spider, Polymers for Advanced Technology, 5:401-410 (1994).
Deible, C. et al., Molecular barriers to biomaterial thrombosis by modification of surface proteins with polyethylene glycol, Biomaterials, 19(20):1885-1893 (1998).
Delong, S. et al., Covalently immobilized gradients of bFGF on hydrogel scaffolds for directed cell migration, Biomaterials, 26(16):3227-3234 (2005).
Du, H. et al., Grafted poly-(ethylene glycol) on lipid surfaces inhibits protein adsorption and cell adhesion, Biochimica et Biophysica Acta,1326(2):236-248 (1997).
Ebenstein, D. et al., Nanomechanical and Microstructural Properties of *Bombyx mori* Silk Films, Materials Research Society Symposium Proceedings, 841:107-112 (2005).
Furuzono, T. et al., Chemical Modification of Silk Fibroin with 2-Methacryloyloxyethyl Phosphorylcholine I. Graft-Polymerization onto Fabric Using Ammonium Persulfate and Interaction Between Fabric and Platelets, Applied Polymer Science, 73:2541-2544 (1999).
Garcia, Andres J., Interfaces to Control Cell-Biomaterial Adhesive Interactions, Advances in Polymer Science, 203:171-190 (2006).
Hellebrekers, B. et al., Effects of five different barrier materials on postsurgical adhesion formation in the rat, Human Reproduction, 15(6):1358-1363 (2000).
Horan, R. et al., In vitro degradation of silk fibroin, Biomaterials, 26(17):3385-3393 (2005).
Kaplan, David, Bioengineering of Materials, Protein Based Materials, (McGrath & Kaplan, eds., Birkhauser, Boston, MA, pp. 103-1331 (1998).
Kapur, T. and Shoichet, M. Immobilized concentration gradients of nerve growth factor guide neurite outgrowth, Journal of Biomedical Materials Research Part A, 68(2):235-243 (2004).
Karageorgiou, V. et al., Bone morphogenetic protein-2 decorated silk fibroin films induce osteogenic differentiation of human bone marrow stromal cells, Journal of Biomedical Materials Research Part A, 71(3):528-537 (2004).
Kim, H. et al., Processing Windows for Forming Silk Biomaterials into a 3D Porous Matrix, Australian Journal of Chemistry, 58:716-720 (2005).
Kiss, E. et al., XPS and wettability characterization of modified poly(lactic acid) and poly(lactic/glycolic acid) films, Journal of Colloid and Interface Science, 245(1):91-98 (2002).
Lee, J. et al., Tissue anti-adhesion potential of ibuprofen-loaded PLLA-PEG diblock copolymer films.,Biomaterials, 26(6):671-678 (2005).
Leventel, I. et al., Soft biological materials and their impact on cell function, Soft Matter, 3:299-306 (2007).
Lim, V. et al., Surface modification of polypyrrole films via grafting of poly(ethylene glycol) for improved biocompatibility, Synthetic Metals, 119:261-262 (2001).
Lucas, F. et al., The silk fibroins, Advanced Protein Chemistry, 13:107-242 (1958).
Luo, Y. and Shoichet, M., Light-activated immobilization of biomolecules to agarose hydrogels for controlled cellular response, Biomacromolecules, 5(6):2315-2323 (2004).
Lv, Q. et al., Clotting times and tensile properties of insoluble silk fibroin films containing heparin, Polymer International, 54:1076-1081 (2005).
Madani, F. et al., PEGylation of microspheres for therapeutic embolization: preparation, characterization and biological performance evaluation, Biomaterials, 28(6):1198-1208 (2007).
Matsumoto, H. et al., Interaction of proteins with weak amphoteric charged membrane surfaces: effect of pH, Journal of Colloid and Interface Science, 264(1):82-88 (2003).
Murphy, A. and Kaplan, D., Biomedical applications of chemically-modified silk fibroin, Journal of Materials Chemistry, 19(36):6443-6450 (2009).
Owens, D. and Peppas, N., Opsonization, biodistribution, and pharmacokinetics of polymeric nanoparticles, International Journal of Pharmaceutics, 307(1):93-102 (2006).
Panilaitis, B. et al., Macrophage responses to silk, Biomaterials, 24(18):3079-3085 (2003).
Pasche, S. et al., Effects of ionic strength and surface charge on protein adsorption at PEGylated surfaces, Journal of Physical Chemistry B, 109(37):17545-17552 (2005).
Puleo, D. and Nanci, A., Understanding and controlling the bone-implant interface, Biomaterials, 20:2311-2321 (1999).
Ratner, B. and Bryant, S., Biomaterials: where we have been and where we are going, Annual Review of Biomedical Engineering, 6:41-75 (2004).
Sannino, A., et al., Polymeric meshes for internal sutures with differentiated adhesion on the two sides, Journal of Materials Science: Materials in Medicine, 16(4):289-296 (2005).
Sofia, S. et al., Functionalized silk-based biomaterials for bone formation, Journal of Biomedical Materials Research, 54(1):139-148 (2001).
Tiller, J. et al., Improving biomaterial properties of collagen films by chemical modification, Biotechnology and Bioengineering, 73(3):246-252 (2001).
Vepari, C. and Kaplan, D., Covalently immobilized enzyme gradients within three-dimensional porous scaffolds, Biotechnology and Bioengineering, 93(6):1130-1137 (2006).
Wilson, C. et al., Mediation of Biomaterial-Cell Interactions by Adsorbed Proteins: A Review, Tissue Engineering, 11(1-2):1-44 (2005).
Wong, J. et al., Balance of chemistry, topography, and mechanics at the cell-biomaterial interface: Issues and challenges for assessing the role of substrate mechanics on cell response, Surface Science, 570:119-33 (2004).

(56) References Cited

OTHER PUBLICATIONS

Wu, Y. et al., Mesenchymal stem cells enhance wound healing through differentiation and angiogenesis, Stem Cells, 25(10):2648-2659 (2007).

Xu, H. et al., Characterizing the modification of surface proteins with poly(ethylene glycol) to interrupt platelet adhesion, Biomaterials, 27(16):3125-3135 (2006).

Zhang, M. et al., Proteins and cells on PEG immobilized silicon surfaces, Biomaterials, 19(10):953-960 (1998).

* cited by examiner

10 # SURFACE MODIFICATION OF SILK FIBROIN MATRICES WITH POLY(ETHYLENE GLYCOL) USEFUL AS ANTI-ADHESION BARRIERS AND ANTI-THROMBOTIC MATERIALS

CROSS REFERENCE TO RELATED APPLICATIONS

This application is a National Phase Entry Application under 35 U.S.C. §371 of co-pending International Application PCT/US2009/064673, filed 17 Nov. 2009, which claims the benefit under 35 U.S.C. 119(e) of U.S. Provisional Application No. 61/115,248, filed Nov. 17, 2008, the contents of which are incorporated herein by reference in its entirety.

GOVERNMENT SUPPORT

This invention was made with government support under EB002520 awarded by the National Institutes of Health. The government has certain rights in the invention.

FIELD OF THE INVENTION

The present invention provides compositions and methods for the production of silk fibroin matrices that are surface-PEGylated on one or more surfaces. Such surface-modified silk fibroin matrices can be used in biomedical applications, such as anti-adhesive and anti-thrombosis materials.

BACKGROUND OF THE INVENTION

Regulation of cell behavior on biomaterials is an essential element of wound repair and tissue engineering. Cell-to-biomaterial surface interactions are critical to the success of biomaterial design. Cell responses, such as attachment and proliferation, are dependent upon the biomaterial surface properties such as topography, surface energy, charge, mechanical properties, and the presence and concentration of cell recognition peptides.

Modification of biomaterial surfaces may be used to convey information to cells without alteration of bulk material properties. Surface modification eliminates the need to blend materials or to synthesize new materials to achieve desired cell responses, which might negatively impact mechanical properties and/or degradation profiles. In addition, FDA-approved biomedical materials can be significantly enhanced by modification of their surfaces; in some cases reducing regulatory hurdles when compared to introducing or altering bulk material features.

Hence, there remains a need for biomaterials with improved surface modifications for use in medical applications.

SUMMARY OF THE INVENTION

The present invention provides for silk fibroin matrices surface-functionalized with poly(ethylene glycol) (PEG) to modify, for example, protein adsorption and cell adhesion and/or proliferation on the surface of the silk fibroin matrices. One embodiment of the present invention is directed to a method of producing a silk fibroin matrix having at least one side surface-modified with PEG. The method comprises providing a silk fibroin matrix, optionally hydrating the silk fibroin matrix; and reacting at least one surface of the silk fibroin matrix with a functional group-activated PEG, such as cyanuric chloride-activated PEG, for a time sufficient for the activated PEG to bind to the surface of the silk fibroin matrix. The silk fibroin matrix may be a silk film, silk tube, silk mat, 3-D silk scaffold, silk fiber, or a silk microsphere. An example is a surface-PEGylated silk fibroin film.

An aspect of the present invention relates to a silk fibroin matrix wherein solely the surface of the silk fibroin matrix is modified by coupling to PEG. More specifically, reactions on a silk film surface with different concentrations of activated PEG generated films with PEG graft densities from 0.02 mg/cm$^2$ to 0.4 mg/cm$^2$ of silk fibroin. Increased PEGylation resulted in increased hydrophilicity as analyzed by contact angle. Increased PEGylation decreased human IgG adsorption; decreased the attachment and proliferation of human fibroblasts and human mesenchymal stem cells (hMSCs); and inhibited human platelet attachment. In a particular embodiment, the PEGylation density of silk film surface of at least about 187.5 µg PEG/cm$^2$ silk maintained anti-adhesion of cells for at least about 15 days. Controlling the degree of PEGylation on surface of silk fibroin matrix also regulates both the degradation rate of the silk fibroin matrix, and the differentiated adhesion of cells or differentiated adsorption of proteins on the surface of the silk matrix.

Another aspect of the present invention relates to a silk fibroin matrix comprising one or more exterior surfaces (e.g., sides) with first exterior surface chemically conjugated to PEG through the methods provided herein. A second exterior surface or the other surfaces of the silk fibroin matrix may be left unmodified or may also be modified by chemically conjugating to PEG. The amount of PEG coupled to the first surface may or may not be the same as the amount of PEG coupled to the second surface or the other exterior surfaces. One particular embodiment of the present invention relates to differentiated surface modification on two or more sides of silk fibroin matrix, which brings differentiated adhesion properties on each of the two or more sides: the unmodified or less-modified surface can be contacted with tissues and promote tissue ingrowth, while the modified side can inhibit or prevent adhesion of tissues to opposing tissues or organs. The silk fibroin matrix may be preloaded, i.e., loaded in bulk solution, with an active agent before being processed into a matrix and surface-modified. Upon surface-modification, the PEGylated silk matrix may be loaded with an active agent, including cells. Because the silk matrix may be selectively modified with different amounts of PEG on different surfaces, the silk matrix may have different active agent-binding capabilities on the different surfaces, providing for preferential active agent loading on each surface. Additionally, the silk fibroin matrix may have a particular degradation profile, controlled by the composition and structure, e.g., β-sheet structure, of the silk fibroin matrix.

The surface-modified silk fibroin matrix of the present invention may be used as a variety of biomaterials such as adhesion barrier materials and thrombotic barrier materials. The surface-PEGylated silk fibroin matrix provided herein can be used to produce a regenerated tissue, medical device, or medical implant for placement in a subject.

The present invention thus also provides for methods of inhibiting adhesions of tissues that are normally separated, or of inhibiting thrombosis.

In one aspect, the method comprises the steps of providing a silk fibroin matrix having at least one surface coupled to PEG, such that protein adsorption and cell adherence is inhibited on that surface; and placing the silk fibroin matrix at a site in need of said adhesion inhibition or thrombosis inhibition.

In the other aspect, the method comprises the steps of providing a silk fibroin matrix having a first surface a second surface, wherein only the first surface has been modified by being coupled to PEG, such that protein adsorption and cell adherence are inhibited on the first surface but are not inhibited on the second surface of the matrix; and placing the silk fibroin matrix at a site in need of adhesion inhibition, such that said first surface inhibits or prevents adhesion of the treated tissues on to opposing tissue surfaces or a tissue-organ surface, and the second surface is contacted with the treated tissues to induce ingrowth of treated tissues. In yet another aspect, the method comprises the steps of providing a silk fibroin matrix having a first surface and a second surface, wherein only the first surface has been coupled to PEG, such that blood protein adsorption and blood cell adherence are inhibited on the first surface but not so inhibited on the second surface of the matrix; and placing the silk fibroin matrix at a site in need of said thrombosis inhibition, such that said first surface is in contact with blood to inhibit or prevent thrombosis, and said second surface is contacted with surrounding tissues to induce ingrowth of said tissues.

The silk fibroin matrix of the present invention may contain at least one active agent to provide more therapeutic benefits to the silk fibroin-based materials. For example, when two sides of silk fibroin matrix are differentiated surface-modified, upon contacting the damaged tissues with the adherent side of the matrix, the active agents on the adherent side may be released to aid or inhibit certain functionalities of the damaged tissues, such as promote cell ingrowth and wound healing of the damaged tissues in contact, while the non-adherent side inhibits or prevents tissue adhesions to the opposing tissues or organs.

DETAILED DESCRIPTION

Figure 1:
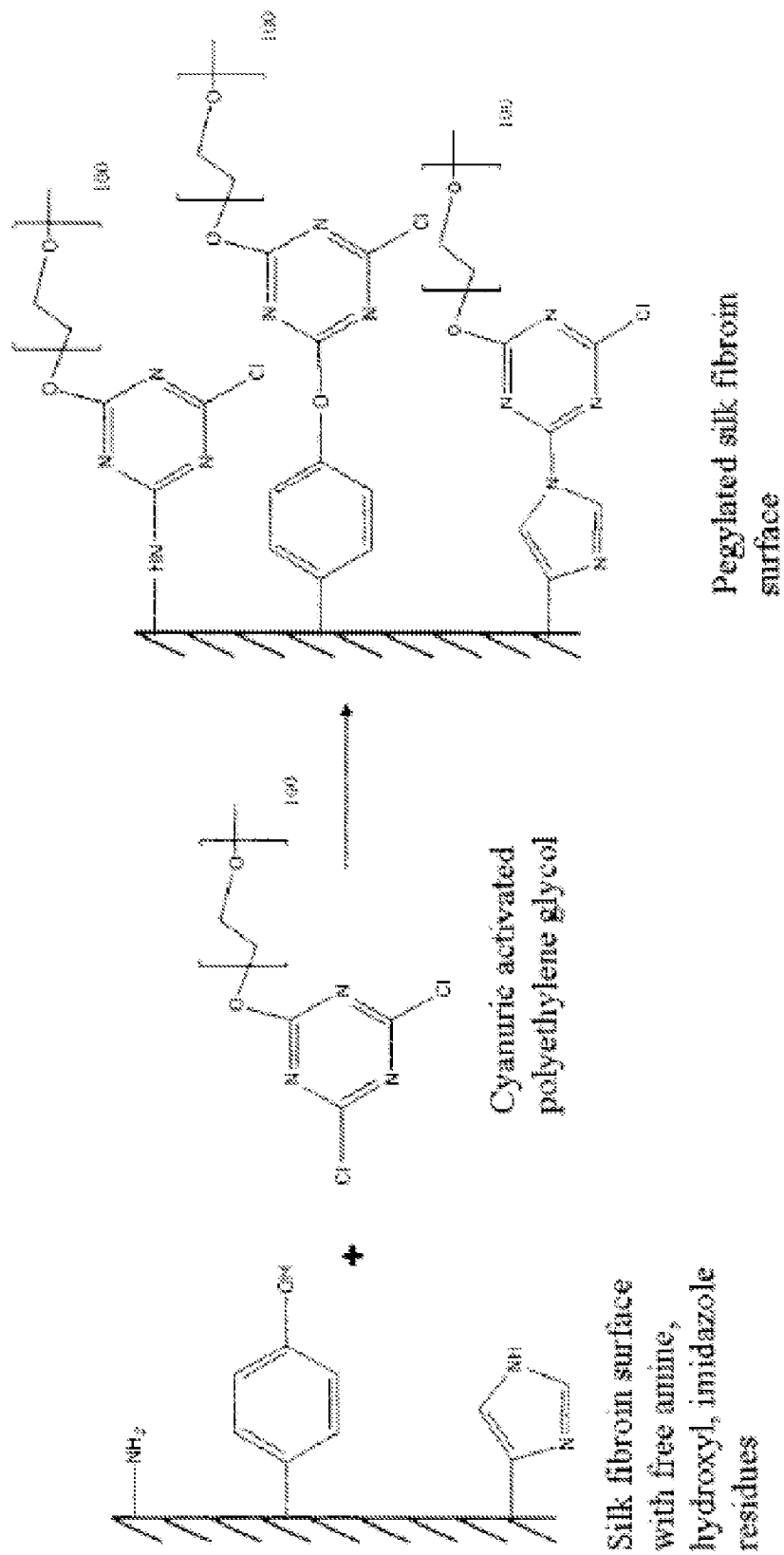
FIG. 1 is a schematic showing the reaction of cyanuric chloride activated poly(ethylene glycol) to side chains of silk fibroin (adapted from Gotoh et al., 4 Bioconjug. Chem. 554-59 (1993)).

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

The present invention provides for silk fibroin matrices surface-functionalized with PEG, which modifies protein and cell interactions with the matrix surface, such as those related to adhesion and proliferation, and affects matrix degradation. More specifically, a functional group-activated PEG is used to modify the surface residues of silk fibroin matrices. For example, cyanuric chloride-activated PEG was used at different concentrations to modulate silk fibroin film surfaces. Varying PEGylation on the films resulted in altered surface wetness, protein adsorption, and cell proliferation. The outcomes suggest options for surface interactions with silk fibroin based biomaterials related to anti-adhesion barriers, anti-thrombosis and related biomedical application.

Regulation of cell behavior on biomaterials is an essential element of wound repair and tissue engineering. Cell-biomaterial surface interactions are critical to the success of biomaterial design. Cell responses such as attachment and proliferation are dependent upon the surface properties such as topography, surface energy, charge, mechanical properties, and the presence and concentration of cell recognition peptides. Wong et al., 570 Surface Sci. 119-33 (2004); Wilson et al., 11(1-2) Tissue Engin. 1-18 (2005); Puleo & Nanci; 20 Biomats. 2311-21 (1999); Garcia, 203 Adv. Polymer Sci. 171-90 (2006); Levental et al., 3 Soft Matter 299-306 (2007).

Additionally, modification of biomaterial surfaces conveys information to cells without the alteration of bulk material properties. Surface modification eliminates the need to blend materials or to synthesize new materials to achieve desired cell responses, which can negatively impact mechanical properties and/or degradation profiles. In addition, characteristics of FDA-approved biomedical materials can be enhanced significantly by surface-modification; in some cases reducing regulatory hurdles when compared to introducing or altering bulk material features. Surface modification also provides for advantageous spatial regulation of cell interactions via localized decorations, such as by immobilizing proteins in gradient patterns on films (Campbell et al., 26 Biomats. 6762-70 (2005)), within hydrogels (DeLong et al., 26 Biomats. 3227-34 (2005); Cao & Shoichet, 103 Neurosci. 831-40 (2001); Kapur & Shoichet, 68 J. Biomed. Mater. Res. A 235-43 (2004); Luo & Shoichet, 5 Biomacromol. 2315-23 (2004)), and within porous scaffolds (Vepari & Kaplan, 93 Biotechnol. Bioeng. 1130-37 (2006)).

Control of protein adsorption and cell attachment is necessary for certain biomedical material applications, such as anti-adhesive barriers which require non-fouling properties. Ratner & Bryant, 6 Ann. Rev. Biomed. Eng. 41-75 (2004). Additionally, anti-adhesive barriers are important for reducing adhesions between traumatized tissues, mostly of abdominal and pelvic origins. Traumatized tissues, such as in the peritoneal cavity and hernias, naturally form adhesions, which can result in chronic abdominal pain and bowel constrictions. Hellebrekers et al., 15 Human Reprod. 1358-63 (2000). The most common preference to reduce adhesions is to provide a mechanical barrier between traumatized tissues, allowing them to regenerate without adhesion formation. The properties of an anti-adhesive barrier include biocompatibility, resistance to protein adsorption and cell growth, mechanical durability, bioresorbability and laparoscopic delivery. Id. Another property of an anti-adhesive barrier material is differential cell adherence on the two sides of the biomaterial. This type of two-sided biomaterial would be invaluable for hernia and intraperitoneal tissue surgeries, where the adherent side is effective on the traumatized surface while the non-adherent side of the biomaterial inhibits or prevents adhesion to the opposing tissue. Id.; Sannino et al., 16 J. Mater. Sci. Mater. Med. 289-96 (2005).

Control over protein adsorption and platelet adsorption is also required for materials that are in contact with blood such as cardiovascular stents, coatings for heart vessels, drug release devices, and vascular grafts. Such materials require structural integrity and resistance to thrombosis for extended periods of time. Furuzono et al., 73 J. Applied Polymer Sci. 2541-44 (1999).

Silk fibroin, a fibrous protein derived, for example, from the cocoon of *Bombyx mori*, is well-known for its unique mechanical properties. Cunniff et al., 5 Polymers for Adv. Tech. 401-10 (1994); Ebenstein, Mats. Res. Soc'y Symp. Proc. 107-12 (2005). Silk fibroin is biocompatible, sterilizable (Panilaitis 24 Biomats. 3079-85 (2003)), and available in a variety of formats (see, e.g., Kim et al., 58 Australian J. Chem. 716-20 (2005)). Long-standing FDA regulatory approval of silk sutures, its abundance as raw fiber material and its controlled proteolytic degradability in vitro and in vivo establish silk fibroin as an important biomaterial. Altman et al., 24 Biomats. 401-16 (2003); Horan et al., 26 Biomats. 3385-93 (2005). The degradability of silk fibroin films and fibers in vitro and the relationship with mechanical properties has also been established. Arai et al., 91 J. Appl. Polymer Sci. 2383-90 (2004).

As a biomaterial, silk fibroin is advantageous for uses as anti-adhesive barriers and anti-thrombotic materials because of its mechanical properties and slow degradation rate. Additionally, the surface properties of polymers can be changed without altering bulk properties, to preserve crystallinity, mechanical and degradation properties. Chan et al., 24 Surface Sci. Rep. 1-54 (1996). For example, surface modification of silk fibroin fibers with various isocyanates did not affect tensile strength. Arai et al., 79 J. Appl. Polymer Sci. 1756-63 (2001). Further, functionalization of silk fibroin fibers with the integrin recognition peptide, RGD, resulted in increased cell attachment. Chen et al., 67 J. Biomed. Mater. Res. A 559-70 (2003). Also, surface modification of silk fibroin by covalent coupling of proteins via carbodiimide chemistry resulted in enhanced mineral formation on silk films when seeded with human bone marrow derived mesenchymal stem cells and osteoblasts. Sofia, 54 J. Biomed. Mater. Res. 139-48 (2001); Karageorgiou et al., 71 J. Biomed. Mater. Res. A 528-37 (2004).

The present invention provides for surface-functionalization of silk fibroin matrices with PEG in order to, inter alia, modify protein adsorption and cell interactions with the surface of silk fibroin matrices related to adhesion and proliferation. Hence one embodiment of the present invention provides for a method of producing a silk fibroin matrix having at least one external surface (i.e., side) modified with PEG. The method comprises providing a silk fibroin matrix, and optionally hydrating the silk fibroin matrix; and reacting at least one exterior surface of the silk fibroin matrix with a functional group-activated PEG for a time sufficient for the activated PEG to bind to the surface of the silk fibroin matrix. Carbodiimide coupling provides one approach for silk-PEG coupling, by binding activated PEG to the surface of silk fibroin matrix is through diazonium coupling reaction, wherein the functional group-activated PEG is PEG substituted diazonium salt. Vepari & Kaplan, 2006; Chen et al., 2003; Murpy & Kaplan, 19 J. Mater. Chem. 6443-50 (2009). Another example of functional group-activated PEG is cyanuric chloride-activated PEG. To increase the reactivity of the surface residues of silk fibroin matrix, the silk fibroin matrix may be activated before coupling reaction with activated PEG. For example, when coupling cyanuric chloride-activated PEG to silk matrix surface, the surface residues of silk matrix may be activated by a basic aqueous solution, such as sodium borate (pH ~9), for a minimum of 30 min. Typical reaction times for cyanuric chloride-activated PEG binding to the surface of silk fibroin matrix ranges from several hours, or 12 hours, to a day, at 4° C., inclusive.

As used herein, the term "fibroin" includes silkworm fibroin and insect or spider silk protein. Lucas et al., 13 Adv. Protein Chem. 107-242 (1958). For example, silk fibroin may be obtained from a solution containing a dissolved silkworm silk or spider silk. The silkworm silk protein is obtained, for example, from *B. mori*, and the spider silk is obtained from *Nephila clavipes*. Alternatively, silk proteins suitable for use in the present invention can be obtained from a solution containing a genetically engineered silk, such as from bacteria, yeast, mammalian cells, transgenic animals or transgenic plants. See, e.g., WO 97/08315; U.S. Pat. No. 5,245,012.

Silk fibroin matrix may be prepared from an aqueous silk fibroin solution, which may be prepared from the silkworm cocoons using techniques known in the art. See, e.g., U.S. patent application Ser. No. 11/247,358; WO/2005/012606; WO/2008/127401. The silk aqueous solution can then be processed into silk fibroin matrices such as silk films, silk tubes (WO 2009/023615), electrospun silk mats (WO 2004/0000915), 3-D silk scaffold such as 3-D silk solid block (WO2003/056297), silk microspheres (PCT/US2007/020789), silk fibers (WO2004/0000915; U.S. Pat. No. 6,902,932). All the above silk fibroin matrices can be used in the present invention for surface-functionalization process, and for biomedical materials applications such as preparation of adhesion barriers and anti-thrombosis materials.

In one embodiment, the silk fibroin matrix used is silk fibroin film, and exemplary method of preparing silk fibroin film having at least one surface modified with PEG comprises the steps of preparing an aqueous silk fibroin solution; lyophilizing the silk fibroin solution; dissolving the lyophilized silk fibroin in hexafluoro-2-propanol (HFIP); drying the dissolved silk fibroin solution to obtain a silk fibroin film; treating said silk fibroin film to induce the formation of β-sheet structure in said film; optionally hydrating the silk fibroin film; and reacting said at least one surface of the silk fibroin matrix with cyanuric chloride-activated PEG for a time sufficient for the activated PEG to bind to the surface of the silk fibroin film.

To achieve the surface-functionalization of silk fibroin matrices, a functional group-activated PEG of molecular weight 5,000 may be used at different concentrations to modulate silk fibroin matrices surfaces. A molecular weight of 5,000 may be suitable because it has been reported as the most effective molecular weight to inhibit protein adsorption and cell proliferation. Du et al., 1326 Biochim. Biophys. Acta 236-48 (1997). Varying PEGylation on the silk fibroin matrix surfaces resulted in altered surface wetness, protein adsorption and cell proliferation. The outcomes suggest options for surface interactions with silk fibroin based biomaterials related to anti-adhesion barriers, anti-thrombosis and related biomedical applications.

The embodiments of present invention thus provide for methods of controlling the degree of PEGylation on surface of silk fibroin matrix, thereby regulating the degradation rate of the silk fibroin matrix. Surface modification has an advantage over bulk modification of polymers, such that materials with different surface properties on the two faces can be generated, while preserving the bulk material properties. Retention of bulk material properties is important in the case of silk fibroin, which has high tensile strength and tailorable degradation properties. Kim et al., 58 Australian J. Chem. 716-20 (2005). Thus, the degradation profile of silk fibroin may be altered due to surface modification with PEG. Silk fibroin degrades proteolytically; hence restriction of protease access to silk fibroin surfaces may be harnessed to alter degradation rates. Increasing the amount of PEGylation of the surface of silk fibroin matrix, enhances the protection of silk fibroin matrix from proteolytic degradation. On the other hand, a silk matrix modified on only one surface (FIG. 12) retains an accessible surface for proteolytic degradation.

Surface modification of inorganic or synthetic polymer substrates with PEG has been used in various contexts, for example, to increase hydrophilicity (Pasche et al., 109 J. Phys. Chem. B 17545-52 (2005)), reduce cell attachment (Lee et al., 26 Biomats. 671-78 (2005)), and inhibit thrombotic reactions (Xu et al., 27 Biomats. 3125-35 (2006)). Several materials, such as collagen, poly (lactic acid), poly (methyl methacrylate), polystyrene and poly (lactic-co-glycolic acid) have been PEGylated Tiller et al., 73 Biotech. Bioeng. 246-52 (2001); Owens & Peppas, 307 Int'l J. Pharm. 93-102 (2006).

In the present invention, a functional group-activated molecular weight 5,000-PEG was used to chemically modify silk fibroin film surfaces. Functional group-activated PEG refers to PEG or PEG derivatives that are activated with functional groups that react with surface residues of silk fibroin, thereby coupling the activated PEG or PEG derivatives to the surface of silk fibroin. In one embodiment, the coupling reaction between the surface of silk matrix and activated PEG may be a carbodiimide coupling reaction. For example, the surface residues of silk fibroin matrix, typically carboxylic acid-containing residues such as aspartic, glutamic acids, or lysine residues, maybe pre-activated with a mixture of water-soluble 1-ethyl-3-(3-dimethylaminopropyl) carbodiimide (EDC) and N-hydroxysuccinimide (NHS) in 2-(N-morpholino)ethanesulfonic acid (MES) or phosphate buffer at pH 6-7, followed by reaction with an amine-activated PEG. Alternatively, amine-containing surface residues such as histindine, lysine or arginine residues, may be coupled with a functional group-activated PEG that is reactive to amine group, for example, a NHS-activated PEG. In another embodiment, the coupling reaction between the surface of silk matrix and activated PEG may be a diazonium coupling reaction. For example, the surface aromatic residues of silk fibroin matrix, such as tyrosine or histidine, may be pre-activated in an aqueous basic solution, such as borate buffer at pH 9, followed by reaction with PEG substituted diazonium salt.

In one embodiment, the surface residues of silk matrix are coupled with activated PEG through cyanuric chloride-activated coupling. Cyanuric chloride is reactive to amine and hydroxyl groups (FIG. 1), but the imidazole group of histidine and the amine group of lysine in were the major amino acids that reacted with cyanuric activated PEG in the silk fibroin. Gotoh et al., 4 Bioconjug. Chem. 554-59 (1993). Histidine and lysine are 0.2% and 0.4% of the amino acids in silk fibroin, respectively. Kaplan et al., in PROTEIN BASED MATS., 103-31 (McGrath & Kaplan, eds., Birkhauser, Boston, Mass. (1998). Although the reaction of silk fibroin and cyanuric chloride-activated PEG was reported previously (Gotoh, 1993; Gotoh et al., 18 Biomats. 267-71, (1997)), that work was done only in bulk solution: the bulk properties of the entire silk fibroin matrix were thus altered, which may negatively impact the mechanical properties and/or degradation profiles of the silk matrix. In the present invention, however, the surface modification of silk fibroin matrix through PEGylation eliminates the need to blend materials or synthesize new materials to achieve desired surface properties or protein and cell interactions, and has additional advantage over bulk modification, such as the differentiated modification of separate surfaces of silk fibroin matrix to control different surface properties.

Figure 2:
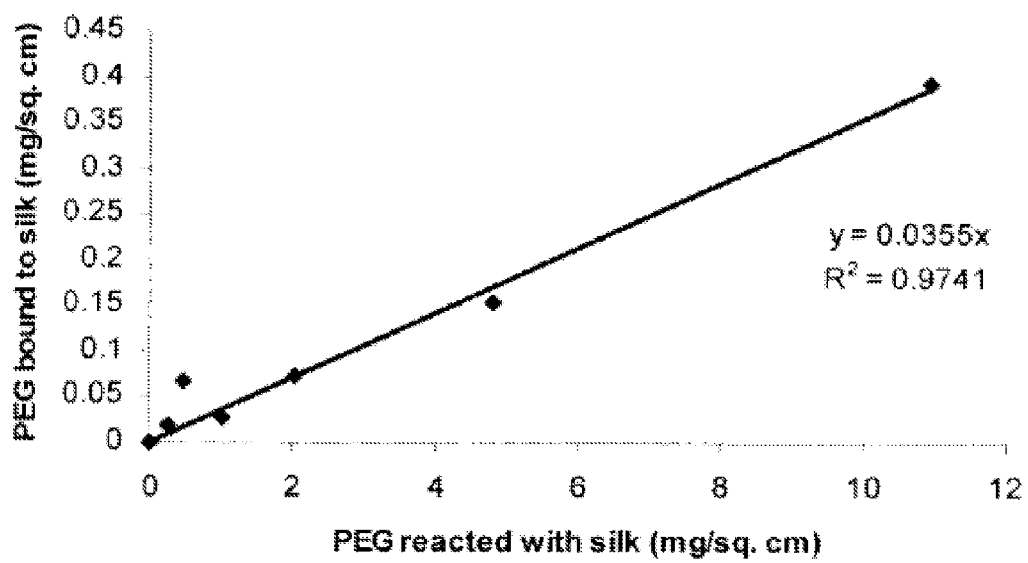
FIG. 2 is a graph showing the linear relationship ($R^2=0.97$) between concentration of PEG reacted with silk fibroin film, and the amount of PEG covalently bound to surface of silk fibroin film.

For example, the concentration of conjugated PEG on silk fibroin was controlled by regulating the concentration of activated PEG used, with reaction time held constant. Increased concentration of activated PEG reacted with silk fibroin films resulted in elevated amounts of PEG coupled to silk fibroin. A linear correlation was found between the concentration of PEG reacted and the amount of PEG coupled per square centimeter of silk fibroin surface (FIG. 2) and a coefficient of determination value of 0.97 was found. Interestingly, PEGylation did not affect the transparency or flexibility of the films.

Figure 3:
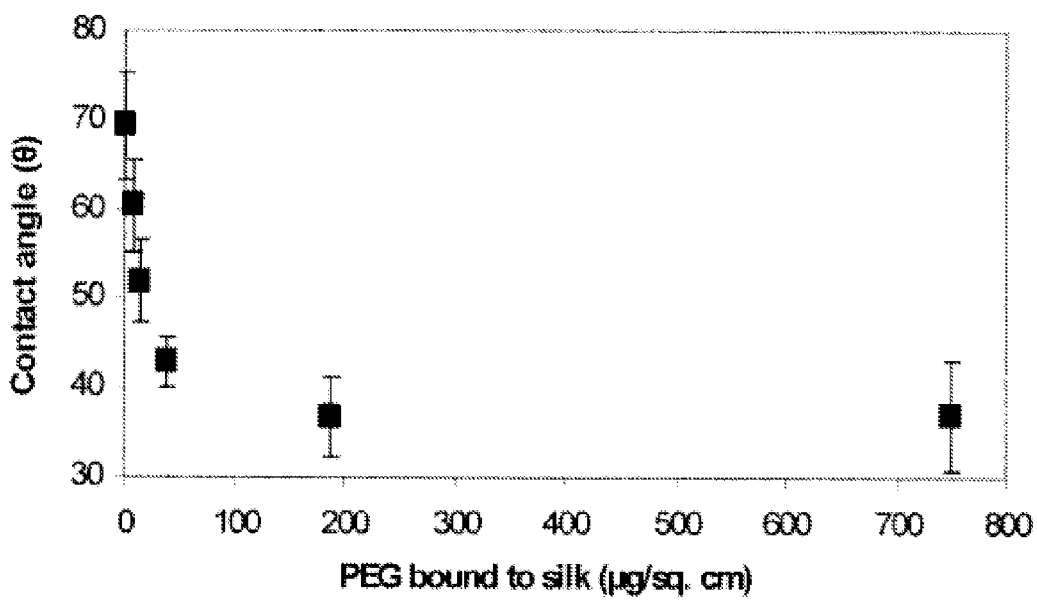
FIG. 3 relates data of water contact angles of silk fibroin films and pegylated silk fibroin films (N=5-8)

The surface energy of PEGylated silk fibroin films were evaluated by water contact angle. Unmodified silk fibroin films had a contact angle of 70 degrees. Increased PEGylation on silk fibroin film surface resulted in decreased water contact angles (FIG. 3). The decrease in water contact angle with increased PEGylation trend was expected as a higher concentration of surface PEGylation results in greater hydration of the surface. Polypyrrole films have also been surface modified by PEG to improve biocompatibility and showed decrease in contact angle with increase in PEG grafting. Lim et al., 119 Synthetic Metals 261-62 (2001). PEO modified PLA and PLGA films showed decrease in water contact angle with increase in PEO. Kiss et al., 245 J. Colloid Interface Sci. 91-98 (2002). Increased PEG content in other polymers, such as polycarbonates and poly(L-lactic acid) have also demonstrated corresponding decreased water contact angles. Lee et al., 2005; Tziampazis et al., 21 Biomats. 511-20 (2000). An increase in surface PEGylation beyond 187.5 μg of PEG per square centimeter of silk fibroin surface did not result in further increase of surface hydrophilicity. This may be due to saturation of available reactive sites for PEGylation, or maximized hydrophilicity at this level of substitution with PEG.

Figure 4:
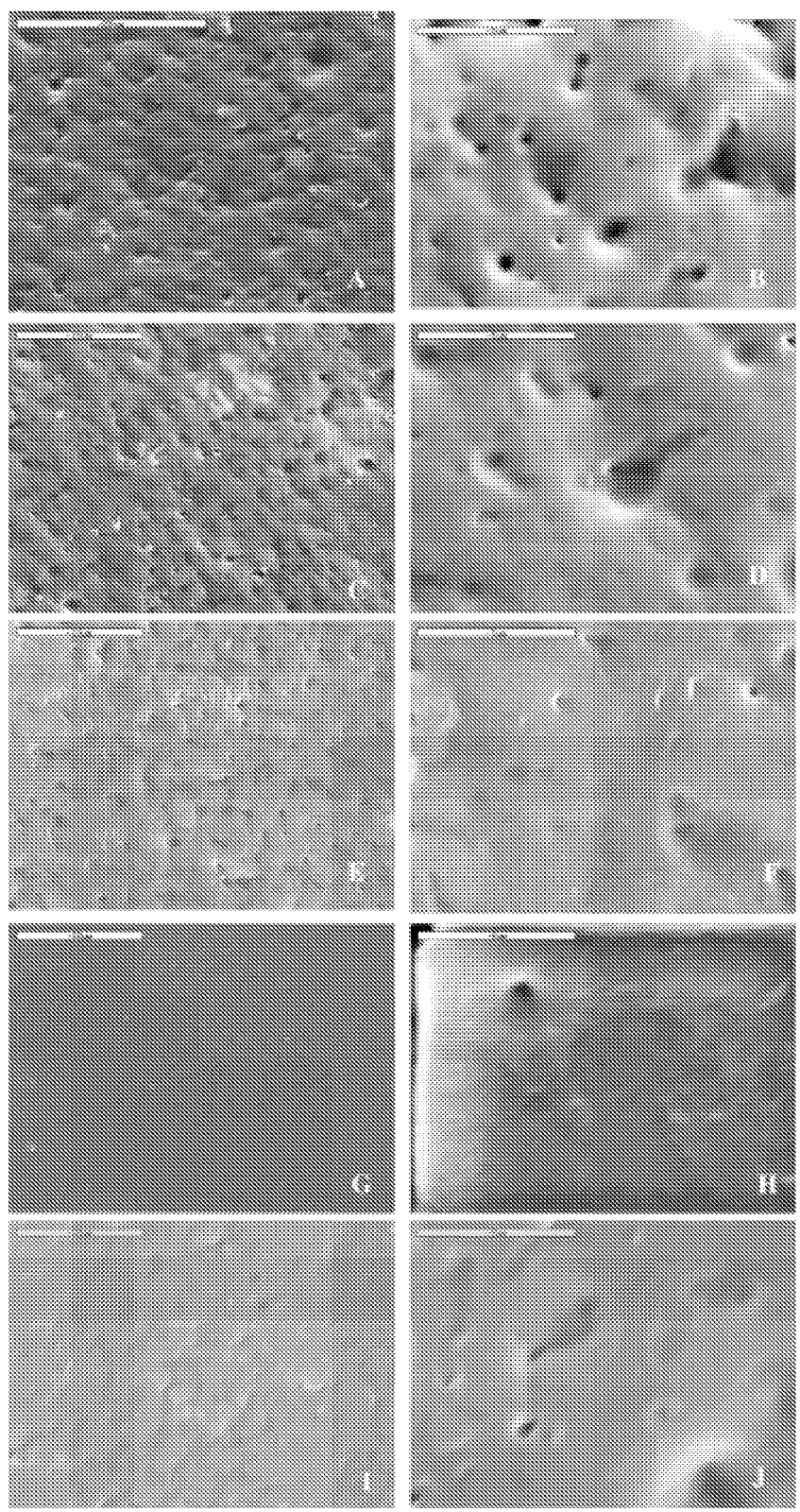
FIGS. 4A to 4J are scanning electron microscopy images of unmodified silk fibroin films and silk fibroin films that are surface modified with PEG. (A, B) Unmodified silk fibroin film; (C, D) Silk films surface modified with 7.5 μg PEG/cm$^2$ silk; (E, F) Silk films surface modified with 37.5 μg PEG/cm$^2$ silk; (G, H) Silk films surface modified with 0.188 mg PEG/cm$^2$ silk; (I, J) Silk films surface modified with 0.75 mg PEG/cm$^2$ silk. Scale bars=20 μm (A, C, E, G, I) and 5 μm (B, D, F, H, J).
Figure 5A:
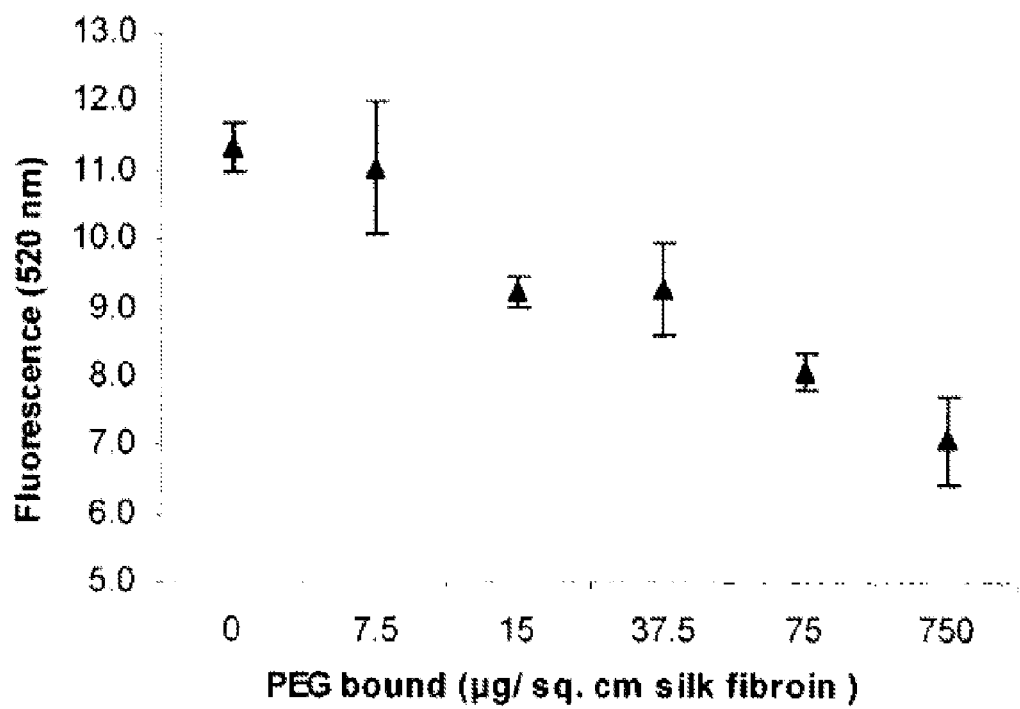
FIG. 5 presents data for protein adsorption of FITC labeled human (A) IgG, and (B) FITC labeled BSA on pegylated silk fibroin films (N=3).
Figure 5B:
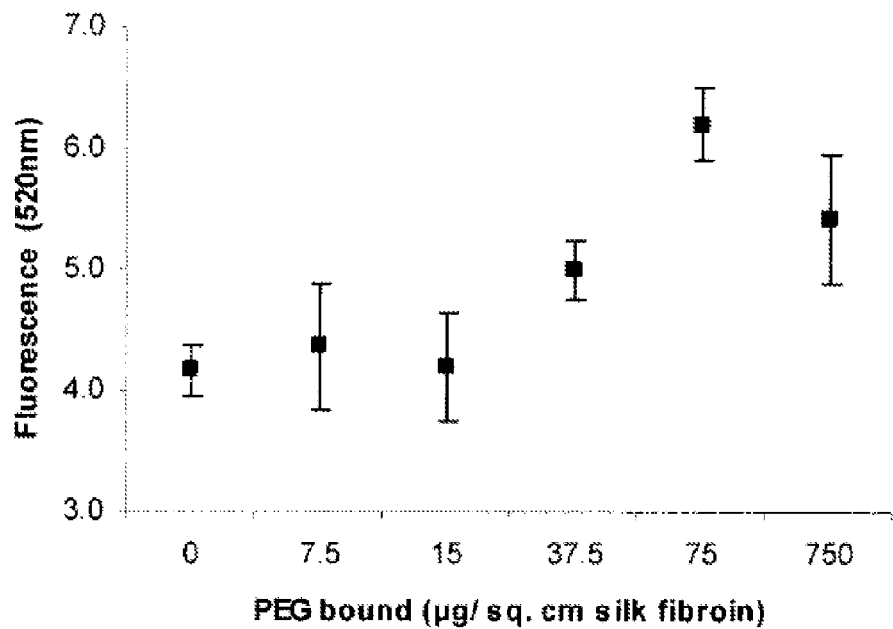

The surfaces of PEGylated silk fibroin films were analyzed by scanning electron microscopy (SEM) to qualitatively determine changes in silk fibroin surface morphology with increase in surface PEGylation (FIG. 4). Unmodified silk film illustrated an uneven surface morphology, similarly as previously reported. Lv et al., 54 Polym. Int. 1076-81 (2005). The various samples analyzed appeared spatially homogeneous, suggesting a uniform PEGylation over the surfaces of silk fibroin films. Increased PEGylation of silk fibroin films resulted in surfaces with smoother morphologies (FIGS. 4B, 4D, 4F, 4H), as was reported when DEAE-Trisacryl® microspheres were PEGylated and processed similarly for SEM. Madani et al., 28 Biomats. 1198-1208 (2007). Silk fibroin film surface modified with 0.188 mg of PEG per square centimeter of silk (FIGS. 4G and 4H) showed the smoothest morphology. An increase of grafted PEG concentration on silk fibroin films from 0.188 mg to 0.75 mg of PEG per square centimeter of silk (FIGS. 4I and 4J) resulted in a slightly rougher morphology. This trend also corresponded with contact angle (FIG. 3) and adsorption of BSA (FIG. 5B). Rougher surface morphology of silk films grafted with 0.75 mg of PEG per square centimeter of silk could be a result of different arrangements of the covalently coupled PEG molecule on the surface. Owens & Peppas, 2006. A different PEG arrangement could result in a decrease in the water content around the PEG molecules and thus generate a slightly rougher morphology.

In the present invention, cell behaviors on silk fibroin surface, such as cell adhesion and proliferation may be regulated by controlling the amount of PEG coupled to the surface of the silk fibroin matrix. Increased PEGylation of silk fibroin surface results in reduced cell attachment and proliferation, and affects cell behavior in, for example, human fibroblasts, bone derived mesenchymal stem cells, and platelets.

Protein adsorption behavior on silk fibroin surface may also be regulated by controlling the amount of PEG coupled to the surface of the silk fibroin matrix. In general, increasing the degree of surface PEGylation of silk fibroin can decrease the adsorption of proteins with larger size, such as antibodies (~150 kDa), and increase the adsorption of proteins with smaller size, such as serum albumin proteins (~70 kDa). Moreover, increased degree of surface PEGylation of silk fibroin may reduce the adsorption of non-polar or non-charged proteins and increase the adsorption of charged proteins. Hence, by controlling the amount of PEG coupled to the surface of silk fibroin matrix, proteins with different sizes and different properties may be differentially adsorbed onto the surface of silk matrix.

In one embodiment, protein adsorption on PEGylated silk fibroin films was explored because PEGylation of polymers has been shown to affect protein adsorption. Increased PEGylation via adsorption, entrapment, or grafting to a biopolymer resulted in higher hydration and decreased protein adsorption. Owens & Peppas, 2006; Tziampazis et al., 2000. In the present invention, the adsorption of human IgG (about 150 kDa) and bovine serum albumin (BSA) (about 69.4 kDa) was evaluated on the PEGylated silk fibroin films. FITC labeled human IgG adsorbed the highest on unmodified silk fibroin (FIG. 4A) and adsorption decreased with increasing PEGylation of the films. A statistically significant difference ($p<0.05$) of adsorbed IgG was found between unmodified silk fibroin film and PEGylated silk fibroin films with 15 μg, 75 μg, and 750 μg of grafted PEG per square cm silk fibroin, respectively.

In contrast, FITC labeled BSA adsorption also changed on films grafted with different amounts of PEGylation, but the trend was opposite to that of the IgG and indicated a general increase in BSA adsorption with an increase in surface PEGylation (FIG. 4B). Statistical difference was found between silk fibroin film with 75 μg PEG/cm$^2$ and silk fibroin films with 7.5 μg, 15 μg, and 37.5 μg of PEG/cm$^2$ silk, respectively. A minor drop in BSA adsorption to lipids grafted with PEG has been reported, with no further decrease in BSA adsorption with increase in PEG content. Du et al., 1326 Biochim. Biophys. Acta 236-48 (1997). It has been suggested that the smaller-sized BSA (about 70 kDa compared to IgG's 150 kDa) "slides" between PEG brushes and adsorb to the fibroin surface. Another explanation of BSA adsorption could relate to the pH of phosphate buffered saline used in the experiments. Additionally, because BSA has a pI of 4.2 and is negatively charged at pH 7 (Matsumoto et al., 264 J. Colloid Interface Sci. 82-88 (2003)), BSA adsorption could increase as the hydrophilic domains in the BSA interact with PEG, thereby increasing adsorption with increasing content of PEG on the surface.

Hence, the present invention provides for the selective loading of small (e.g., BSA) or large (e.g., IgG) loading on a silk fibroin matrix, controlled by the amount of PEGylation on the selected surface of the silk fibroin matrix.

Figure 6:
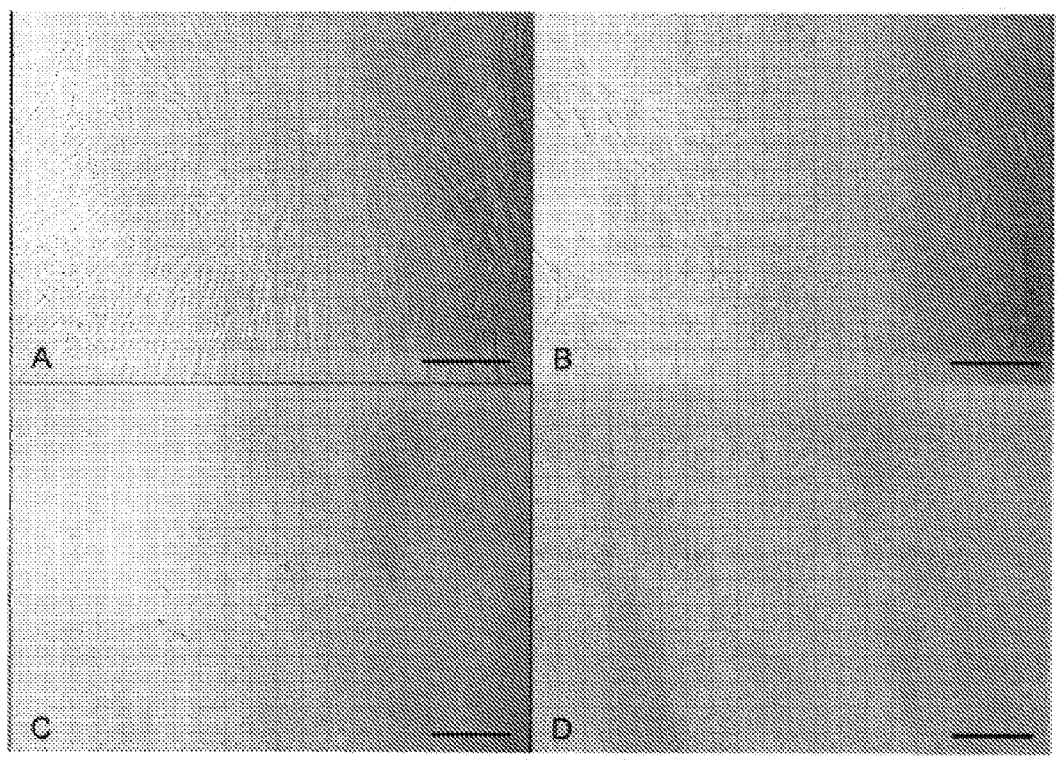
FIGS. 6A to 6D are micrographs evidencing human lung fibroblast (IMR-90) proliferation on silk films after four days. (A) unmodified silk fibroin film; (B) silk fibroin film PEGylated with 37.5 μg PEG/cm$^2$ silk; (C) silk fibroin film PEGylated with 75 μg PEG/cm$^2$ silk; (D) silk fibroin film PEGylated with 375 μg PEG/cm$^2$ silk. Scale bars=200 μm.

In another embodiment, cell adhesion to PEGylated silk fibroin was explored to examine the non-fouling nature of the PEGylated silk fibroin. Human lung fibroblasts were used to evaluate adhesion to PEGylated silk fibroin films. The cells on silk fibroin samples with 7.5 µg to 37.5 µg of PEG per square centimeter of silk showed a spindle shaped morphology. Samples with higher PEGylation showed no cell attachment and rounded cell morphologies after the first day of seeding. At day 4, fibroblast proliferation was assessed by light microscopy (FIG. 5) and alamar blue analysis (FIG. 6). Fibroblast cell proliferation decreased with the increased amount of PEGylation, but this was not statistically lower than unmodified silk until 37.5 µg of PEG was coupled per square centimeter of silk film. Fibroblast attachment and proliferation significantly decreased between 37.5 µg to 75 µg of PEG per square centimeter of silk and remained unchanged with any further increases in PEGylation. These results may be explained by increased hydration of PEGylated silk fibroin surfaces resulting in reduced fibroblast attachment and proliferation, consistent with the observations of others regarding silicon surfaces. Zhang et al., 19Biomats. 953-60 (1998).

Figure 7:
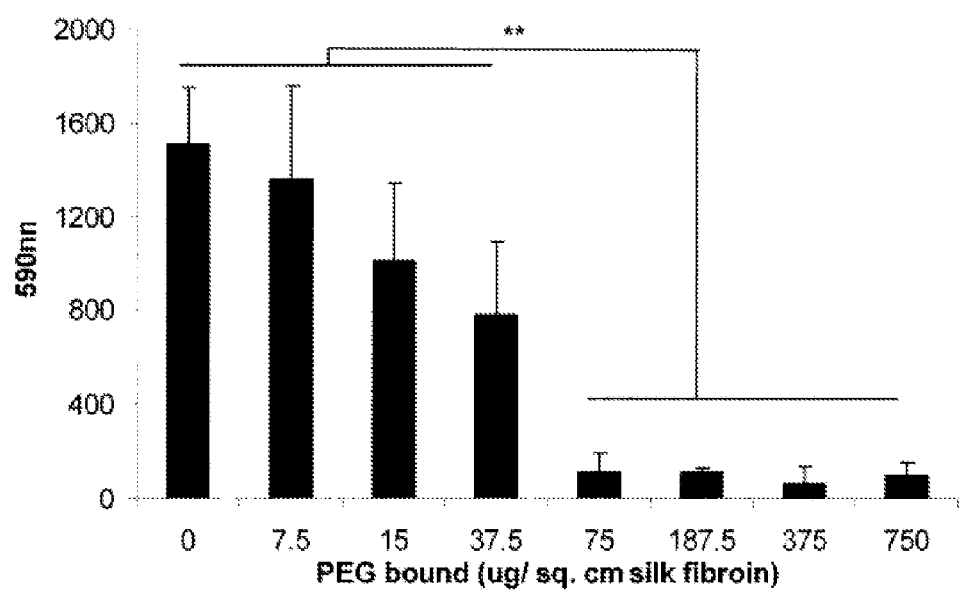
FIG. 7 graphically depicts alamar blue analysis of fibroblast proliferation on PEGylated silk fibroin films (N=3-4). Significant difference found between first and last four groups (**$p<0.01$).
Figure 8:
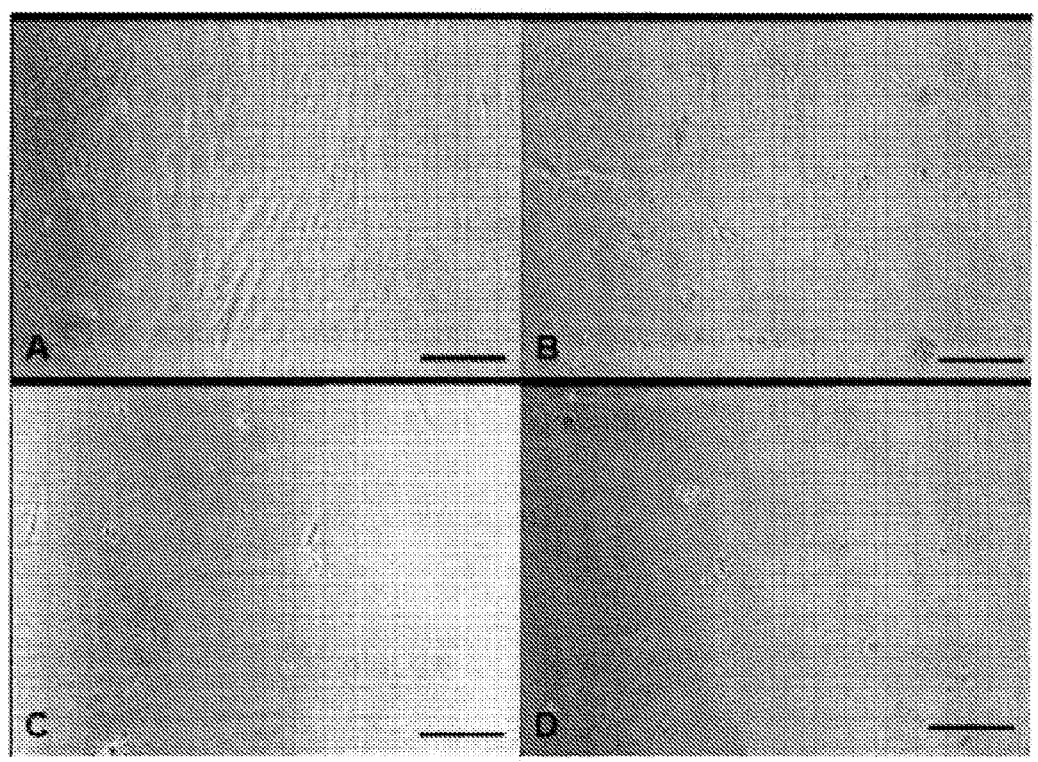
FIGS. 8A to 8D are micrographs evidencing human mesenchymal stem cell proliferation after four days. (A) unmodified silk fibroin film; (B) silk fibroin film PEGylated with 37.5 μg PEG/cm$^2$ silk; (C) silk fibroin film PEGylated with 187.5 μg PEG/cm$^2$ silk; (D) silk fibroin film PEGylated with 750 μg PEG/cm$^2$ silk. Scale bars=200 μm.

Further regarding cell adhesion, mesenchymal stem cells are a common progenitor for several types of cells. Bianco et al., 19 Stem Cells 180-92 (2001). Circulating MSCs are involved in wound healing and respond to traumatized tissues by attachment and differentiation. Wu et al., 25 Stem Cells, 2648-59 (2007). For anti-adhesive applications, reduced MSC attachment and proliferation is important. Hence, the response of hMSCs was investigated on unmodified and PEGylated silk fibroin silk films. hMSC attachment and proliferation was assessed by light microscopy and alamar blue assay. Unmodified films showed the highest proliferation (FIG. 7A), followed by silk films PEGylated by 37.5 µg, 187.5 µg, and 750 µg bound PEG (per square centimeter of silk), respectively. A rounded cell morphology was observed on films with the highest level of PEGylation (FIG. 7D) whereas a fibroblast-like morphology was observed on unmodified silk fibroin film (FIG. 7A) and films PEGylated with 37.5 µg of PEG per square centimeter of silk (FIG. 7B). The same trend observed by light microscopy was reflected by the alamar blue assay. Increased PEGylation on silk fibroin films lead to decreased hMSC attachment and proliferation (FIG. 8). A small increase in bound PEG (7.5 µg of PEG per square centimeter of silk) resulted in a dramatic reduction (statistically different) in hMSC attachment and proliferation. Silk fibroin modified with 75 µg of PEG per square centimeter of silk resulted in the lowest cell proliferation and a further increase in PEG concentration resulted in negligible cell attachment.

Attachment and proliferation of fibroblasts and hMSCs on PEGylated silk fibroin films resulted in similar patterns. Attachment and proliferation of fibroblasts was higher on silk with low PEGylation (7.5 µg and 15 µg of PEG per square centimeter of silk) compared with hMSCs. Differential attachment of cells to the same concentration of grafted PEG on the silk fibroin surface might be due to the reduced number of integrin receptors on hMSCs compared with fibroblasts. As a result, controlled PEGylation of silk fibroin films can differentially modulate attachment and proliferation of two different types of human cells.

Figure 9:
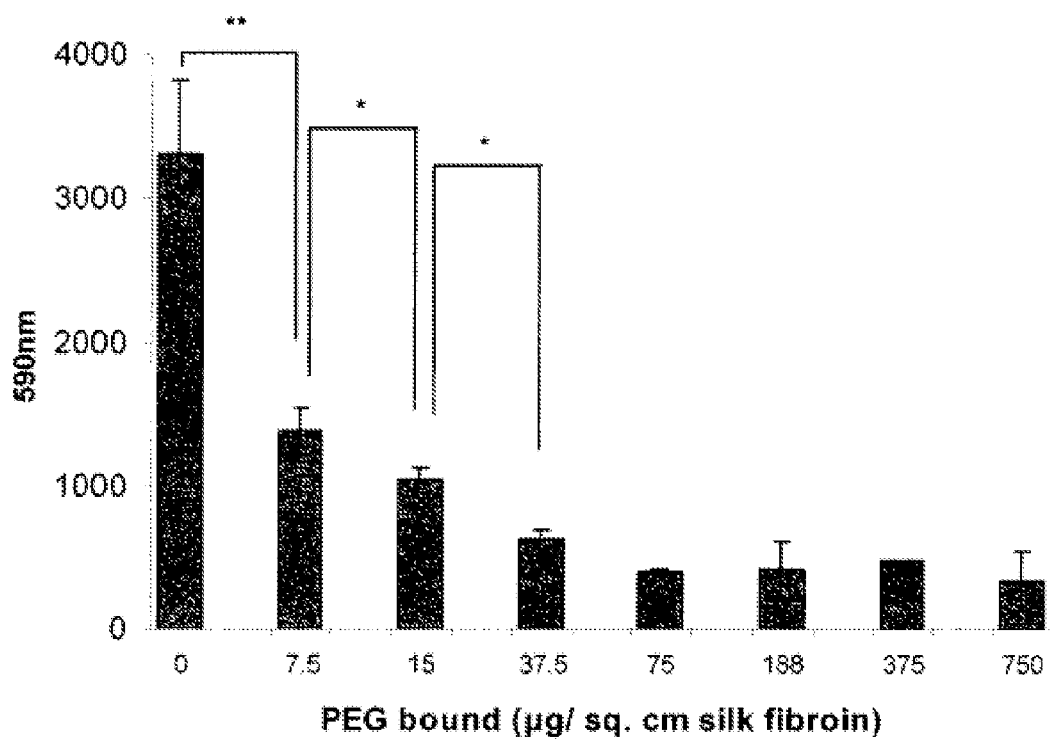
FIG. 9 graphically depicts alamar blue analysis of mesenchymal stem cell proliferation on PEGylated silk fibroin films (N=3-6). Statistical difference (**$p<0.01$ and *$p<0.05$) was found between samples.
Figure 10:
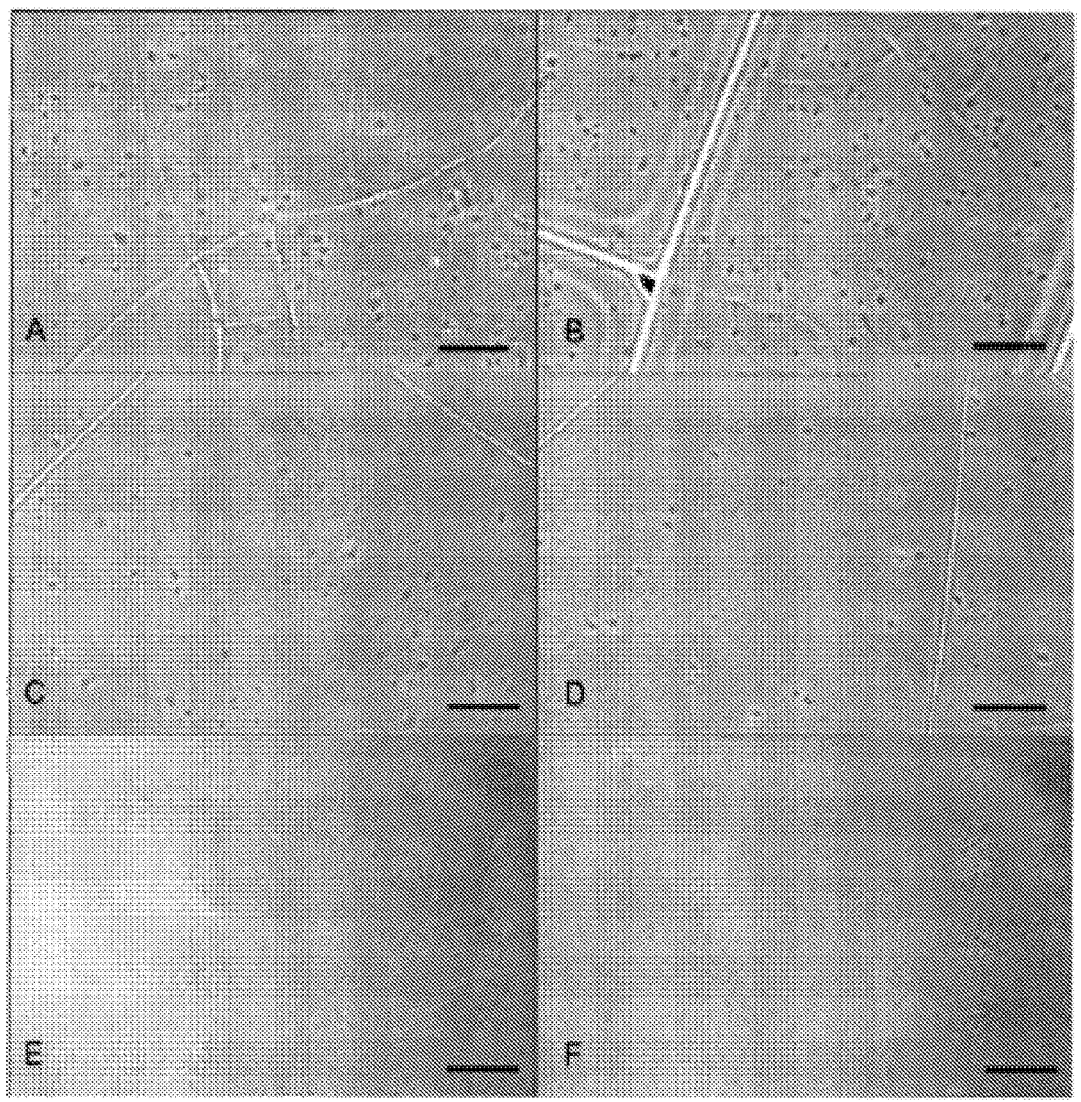
FIGS. 10A to 10F are micrographs showing the attachment of human platelets to (A) unmodified silk fibroin film; (B) silk fibroin film PEGylated with 7.5 μg PEG/cm$^2$ silk fibroin film; (C) silk fibroin film PEGylated with 37.5 μg PEG/cm$^2$ silk fibroin film; (D) silk fibroin film PEGylated with 75 μg PEG/cm$^2$ silk fibroin film, (E) silk fibroin film PEGylated with 375 μg PEG/cm$^2$ silk fibroin film; and (F) silk fibroin film PEGylated with 750 μg PEG/cm$^2$ silk fibroin film (n=3). Light lines in some of the images are cracks in some of the films. Scale bars=50 μm.

Attachment of human platelets to PEGylated silk fibroin films was also explored, because reducing thrombosis is important for biomaterials that are in contact with blood. Blood cells adhere to biomaterials coated with blood proteins. For PEGylated silk fibroin to be useful as a barrier material for wound repair, reduction of attachment of human platelets is necessary. Fresh human platelet rich plasma was allowed to react with unmodified and PEGylated silk fibroin films. Adhered platelets were assessed by light microscopy (FIG. 9). Human platelets adhered to unmodified silk fibroin films and were found to be approximately three times more than the number of platelets adhered to silk fibroin fabrics. Furuzono et al., 73 J. Applied Polymer Sci. 2541-44 (1999). An increase in PEGylation of silk fibroin films resulted in lower platelet adhesion. No significant decrease in platelet attachment was observed until the concentration of PEG on the surface was 187.5 µg of PEG per square centimeter of silk (FIG. 10).

Platelet adhesion on PEGylated silk fibroin film ($5 \times 10^4$ platelets per square centimeter) was comparable to platelet adhesion to silk fibroin fabric coupled with 2-methacryloyloxyethyl phosphorylcholine, an inhibitor of platelet adhesion ($1 \times 10^4$ platelets per square centimeter). Furuzono et al., 1999. The methods of determining adhered platelets were different, however, as Furuzono used lactose dehydrogenase assay for assessing adhered platelets (id.) versus the direct counting of giemsa stained platelets used in the present application.

Compared with PEG-modified silk fibroin ($5\text{-}26 \times 10^4$ adhered platelets per square centimeter), PEG modified polytetrafluoroethylene (PTFE) and preclotted Dacron (Deible et al., 19 Biomats. 1885-93 (1998)), had platelet-binding ranging from $2\text{-}65 \times 10^4$ to $25\text{-}225 \times 10^4$ adhered platelets per square centimeter. Different methods to evaluate adhered platelets were used, however. Radiolabeled platelets were used for assessing on PTFE and Dacron, versus the giemsa stained adhered platelets as used in the present approach; and perfusion was used for PTFE and Dacron (id.) versus static conditions at 37° C. in this study.

Figure 11:
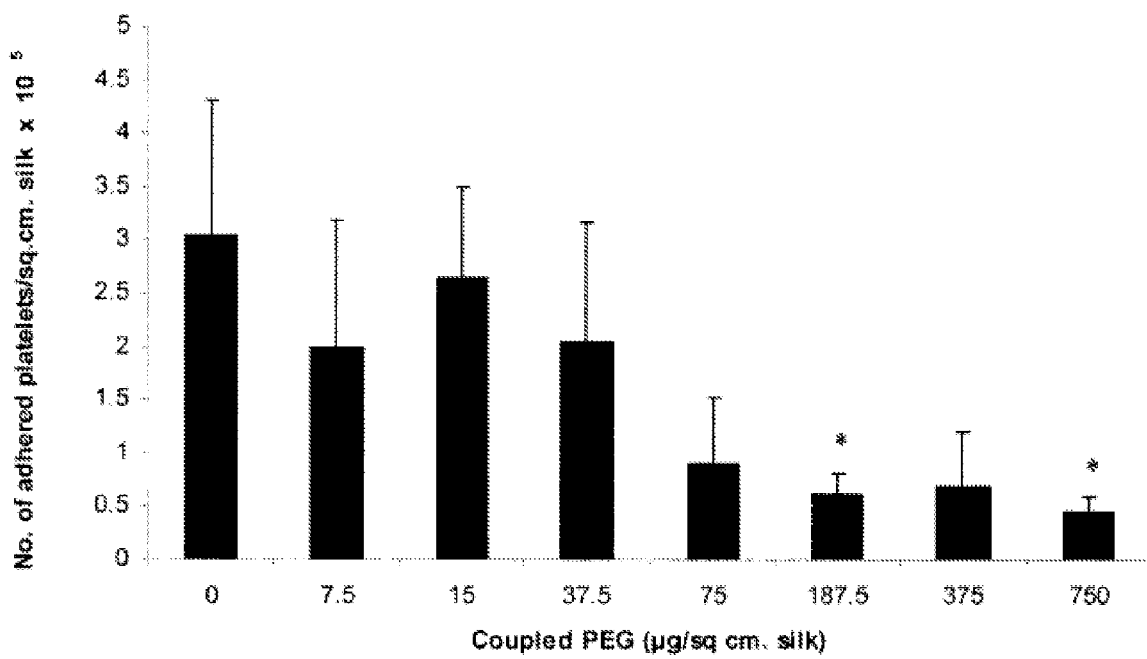
FIG. 11 is a bar graph comparing the number of platelets attached to unmodified silk fibroin and pegylated silk fibroin films of different concentrations of PEG (N=9). Statistical difference (*$p<0.05$) was found between samples and 0 μg, 7.5 μg, 15 μg, and 37.5 μg PEG/cm$^2$ silk fibroin film samples.

Proliferation of fibroblasts on PEGylated silk fibroin films was assessed, because anti-adhesive barriers should sustain non-fouling properties for longer periods of time to allow time for tissue repair. To investigate long-term non-fouling properties of PEGylated silk fibroin, fibroblasts were maintained on modified silk fibroin films for fifteen days. Determined by alamar blue assay, all groups showed an increase in relative proliferation from day four to day fifteen of culture (FIG. 11). Fibroblasts cultured on unmodified silk films continued to proliferate resulting in cell layers. Silk fibroin modified with 75 µg of PEG per square centimeter of silk had the largest difference in cell proliferation from day four to day fifteen, likely due to gradual adsorption of serum proteins onto the film. Silk fibroin PEGylated with 187.5 µg of PEG per square centimeter of silk did not result in significant fibroblast cell proliferation from day four to day fifteen. Thus, silk fibroin films PEGylated with higher concentrations of PEG resisted fibroblast proliferation over two weeks.

The silk fibroin matrix used in the present invention may be modified to contain at least one active agent. The active agent(s) may be loaded to the bulk of silk fibroin matrix by mixing with a silk fibroin solution prior to forming the silk fibroin matrix. The active agent may also be deposited onto the surface of silk fibroin matrix after it is formed and before the surface-PEGylation. Alternatively, the active agent may also be deposited onto the surface of silk fibroin matrix after the surface-PEGylation of silk fibroin matrix. For example, if silk fibroin matrix has more than one side, and at least one side is not surface-modified by PEG, then loading the active agent after the surface PEGylation may deposit the active agent onto the unmodified side of silk fibroin matrix. As another example, if the active agent has certain affinity to PEG, such as proteins with small size or small molecules or charged proteins or molecules, loading the active agent after the surface PEGylation may deposit the active agent onto both modified and unmodified sides of silk fibroin matrix.

The variety of active agents that can be used in conjunction with the silk fibroin matrix of the present invention is vast. For example, the active agent may be a therapeutic agent or biological material, such as cells (including stem cells), proteins, peptides, nucleic acids (DNA, RNA, siRNA), nucleic acid analogues, nucleotides, oligonucleotides or sequences, peptide nucleic acids, aptamers, antibodies or fragments or portions thereof, hormones, hormone antagonists, growth factors or recombinant growth factors and fragments and variants thereof, cytokines, enzymes, antibiotics or antimicrobial compounds, anti-inflammation agent, viruses, antivirals, toxins, prodrugs, chemotherapeutic agents, small molecules, drugs and combinations thereof. Exemplary active agent suitable for modifying the silk fibroin matrix of the present invention includes cells (including stem cells), erythropoietin (EPO), YIGSR peptides, glycosaminoglycans (GAGs), hyaluronic acid (HA), integrins, selectins and cadherins; analgesics and analgesic combinations; steroids; antibiotics; insulin; interferons α and γ; interleukins; adenosine; chemotherapeutic agents (e.g., anticancer agents); tumor necrosis factors α and β; antibodies; cell attachment mediators, such as RGD or integrins, or other naturally derived or genetically engineered proteins, polysaccharides, glycoproteins, cytotoxins, prodrugs, immunogens, or lipoproteins.

One or more active agents may be used to modify the silk fibroin matrix. For instance, when using silk matrix of the present invention as a platform to support biological material such as cells, it may be desirable to add other materials to promote the growth of the agent, promote the functionality of the agent after it is released from the silk fibroin matrix, or increase the agent's ability to survive or retain its efficacy during the processing period. Exemplary materials known to promote cell growth include, but not limited to, cell growth media, such as Dulbecco's Modified Eagle Medium (DMEM), fetal bovine serum (FBS), non-essential amino acids and antibiotics, and growth and morphogenic factors such as fibroblast growth factor (e.g., FGF 1-9), transforming growth factors (TGFs), vascular endothelial growth factor (VEGF), epidermal growth factor (EGF), platelet derived growth factor (PDGF), insulin-like growth factor (IGF-I and IGF-II), bone morphogenetic growth factors (e.g., BMPs 1-7), bone morphogenetic-like proteins (e.g., GFD-5, GFD-7, and GFD-8), transforming growth factors (e.g., TGF-α, TGF-β I-III), nerve growth factors, and related proteins. Growth factors are known in the art, see, e.g., Rosen & Thies, Cellular & Mol. Basis Bone Formation & Repair (R. G. Landes Co.). Additional material to be embedded in silk fibroin matrix may include DNA, siRNA, antisense, plasmids, liposomes and related systems for delivery of genetic materials; peptides and proteins to active cellular signaling cascades; peptides and proteins to promote mineralization or related events from cells; antimicrobial peptides; and proteins and related compounds.

Embedding a bioactive agent in the silk fibroin matrix enables the delivery of active agents in a controlled released manner. Maintaining the bioactive agent in an active form throughout the process of embedding the agent in the silk enables it to be active upon release from the silk matrix. Controlled release of the active agent permits active agent to be released sustainably over time, with controlled release kinetics. In some instances, the bioactive agent is delivered continuously to the site where treatment is needed, for example, over several weeks. Controlled release over time, for example, over several days or weeks, or longer, permits continuous delivery of the bioactive agent to obtain preferred treatments. The controlled delivery vehicle is advantageous because it protects the bioactive agent from degradation in vivo in body fluids and tissue, for example, by proteases.

Controlled release of the active agent from the silk matrix may be designed to occur over time, for example, over 12 hours or 24 hours. The time of release may be selected, for example, to occur over a time period of about 12 hours to 24 hours; about 12 hours to 42 hours; or, e.g., about 12 to 72 hours. In another embodiment, release may occur for example on the order of about 1 day to 15 days. The controlled release time may be selected based on the condition treated. For example, longer times may be more effective for wound healing, whereas shorter delivery times may be more useful for some cardiovascular applications.

Controlled release of the active agent from a silk matrix in vivo may occur, for example, in the amount of about 1 ng to 1 mg/day, inclusive. In other embodiments, the controlled release may occur in the amount of about 50 ng to 500 ng/day, inclusive, or, in another embodiment, in the amount of about 100 ng/day. Delivery systems comprising therapeutic agent and a carrier may be formulated that include, for example, 10 ng to 1 mg therapeutic agent, or about 1 μg to 500 μg, or, for example, about 10 μg to 100 μg, inclusive, depending on the therapeutic application.

The surface-modified silk fibroin matrix of the present invention may also be incorporated into another biopolymer delivery system (e.g., a sponge), or may incorporate other biopolymer structures (e.g., microparticles or nanoparticles) within it. The biopolymer structures may comprise silk fibroin. These composite systems, in which component parts may be selectively loaded with active agent(s), provide another level of control over sustained release and biomaterial structure.

With controlled protein adsorption and controlled cell adhesion and proliferation, the surface-PEGylated silk fibroin matrix of the present invention may be used as a variety of biomaterials such as adhesion barrier materials and thrombotic barrier materials. The surface-PEGylated silk fibroin matrix provided herein can be used to produce a regenerated tissue, medical device or medical implant for placement in a subject. Exemplary regenerated tissues, medical devices or medical implants include, but are not limited to, implantable prosthesis and artificial organs, such as skin, heart, lungs, liver and kidneys; wound healing devices, grafts, patches, sutures, and dressings; vascular repair devices, stents, catheters, grafts, patches, sutures, and dressings; heart valves and pacemakers; and drug release or delivery devices. For example, surface-PEGylated silk microspheres can be used in therapeutic embolization as an embolic agent to devascularize the embolic region away from blood circulation. In another example, surface-PEGylated silk film can be used as wound healing patch that is applied to damaged tissues to separate the damaged tissues from opposing tissues or organs while they heal. In another example, surface-PEGylated silk tube can be used as vascular stent to inhibit thrombus formation and subsequent restenosis and to assure relatively unobstructed blood flow through the vessel.

The present invention also provides for a silk fibroin matrix comprising one or more sides, with the surface of the first side chemically conjugated to PEG through the methods provided herein. The surface of the second side or the other sides of the silk fibroin matrix may be left unmodified or may also be modified by chemically conjugating to PEG. The amount of PEG coupled to the surface of the first side may or may not be the same as the amount of PEG coupled to the surface of the second side or the other sides. Hence the surface of silk fibroin matrix may be evenly and equally modified on all sides, or one or more sides of silk fibroin matrix may be differentiated modified through PEGylation, depending on applications.

Differentiated surface modification of silk matrix by PEGylation can be accomplished by various means: the amount of PEG coupled to the surface of one side can be different from the amount of PEG coupled to the surface of the other side, for example, the degree of PEGylation on a second side is less than the degree of PEGylation on a first side; or one side of silk fibroin matrix is PEGylated and the other side is not PEGylated. Differentiated surface modification through PEGylation results in distinct adhesion properties on two or more sides of silk fibroin matrix: the unmodified side or less-modified side can be placed in contact with traumatized tissues and promote tissue ingrowth, while the PEG-modified side can inhibit or prevent adhesion of damaged tissues to the opposing tissues or organs. Such materials can be used to avoid post-surgical tissue injury due to the tissue adhesions. For example, biomaterials that adhere to the injured surface but are non-adherent to the opposing tissue can be useful in hernia and peritoneal surgeries. Hellebrekers et al., 15 Human Reprod. 1358-63 (2000).

Figure 12:
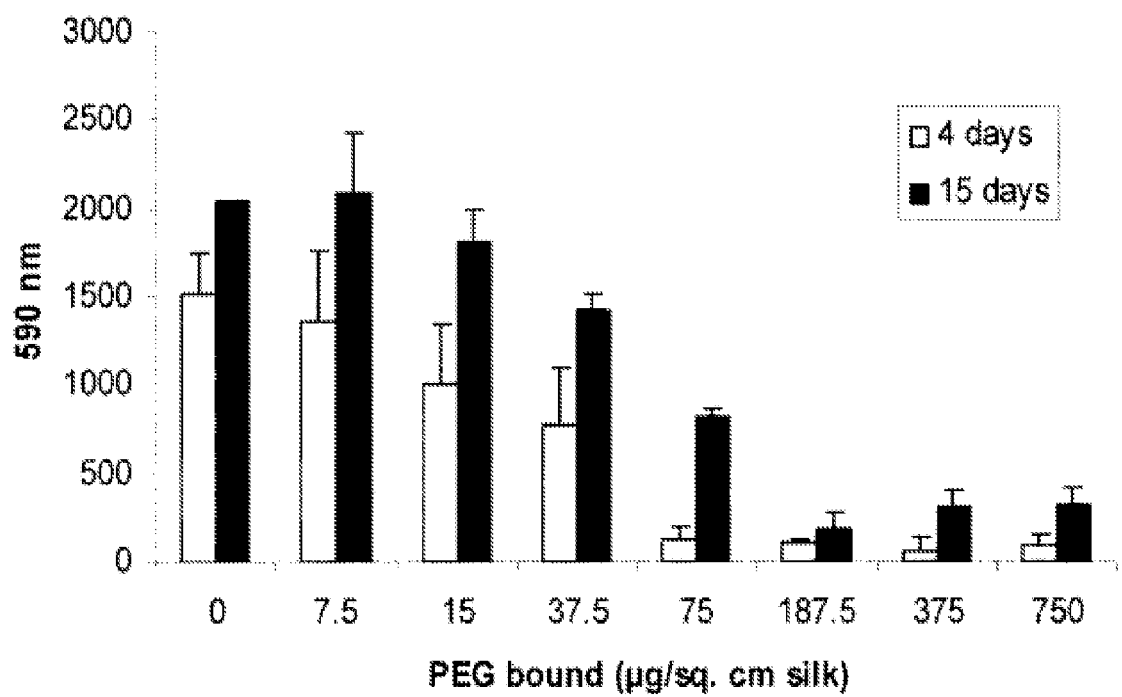
FIG. 12 is a bar graph depicting alamar blue analysis of comparative growth between four and fifteen day culture of fibroblasts on unmodified and pegylated silk fibroin films (N=3 except for unmodified silk fibroin sample at fifteen days (0 μg PEG/cm$^2$, where N=2).
Figure 13:
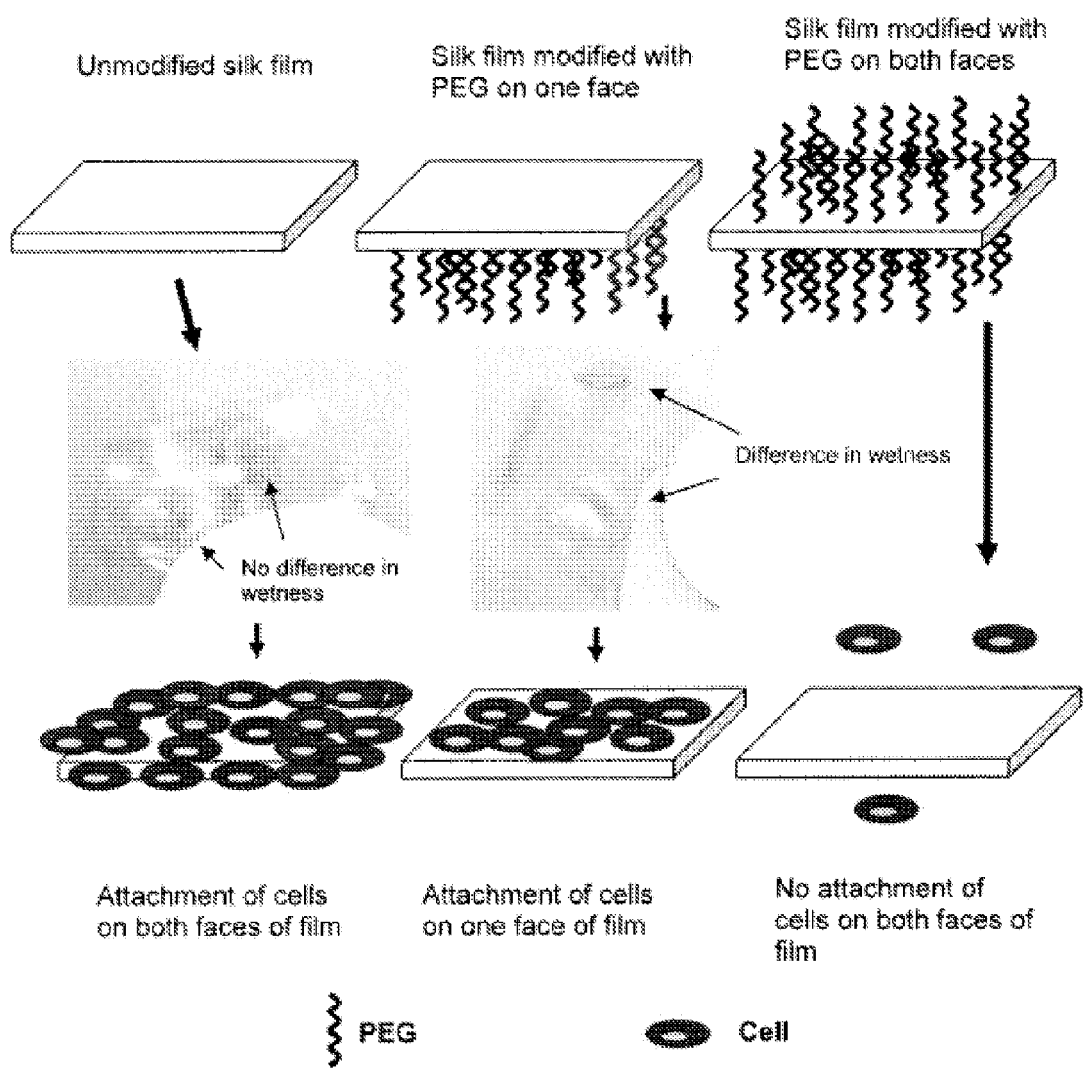
FIG. 13 is an illustration of the control of pegylation to one or both faces of silk fibroin film (as shown by contact angle).

In a particular embodiment, differential adhesion of fibroblasts on two surfaces (sides) of a silk fibroin film was achieved. This strategy prepared a biomaterial with different adhesion properties on its different surfaces by limiting PEGylation to just one side of a silk fibroin film. FIG. 12 shows qualitative differences in contact angle between the PEG-modified and unmodified sides of silk fibroin film relating to differences in cell adhesion and yielding a biomaterial with different adhesion properties on different sides.

The wound healing process involves, essentially, repair or replacement of damaged tissues. One of the complications in this process is the formation of adhesions. The formation of adhesions between tissues or organs of the abdominal or pelvic cavities is a frequent and undesirable complication of abdominal and pelvic surgery. Adhesions in abdominal and pelvic cavities can cause a number of further complications, such as intestinal obstruction, chronic pelvic pain, voiding dysfunction, and infertility. The embodiments of the present invention thus provide for methods of inhibiting or preventing adhesions of tissues that are normally separated. The adhesions to be avoided may be caused by post-operative surgery, such as peritoneal, pericardial, abdominal, obstetric, laparoscopic, endoscopic, gynecological, neurosurgical, ENT, dental, arthroscopic, orthopedic, plastic, reconstructive, prosthetic, muscle or tendon surgery; presence of a foreign body at the site, such as insulin pumps; inflammation of tissues or organs, such as pelvic inflammatory disease; trauma of tissues or organs; irradiation of tissues or organs; presence of a tumor at the site; or administration to the site a drug, such as cyclosporine, that is capable of inducing an adhesion.

In one aspect, the method comprises providing a silk fibroin matrix having at least one surface of the matrix modified by being coupled to PEG, such that protein adsorption and cell adherence is inhibited on the surface; and placing the PEGylated silk fibroin matrix at a site in need of such adhesion inhibition.

In another aspect, the method comprises providing a silk fibroin matrix having at least a first surface and a second surface, wherein the first surface has been modified by being coupled to PEG, such that protein adsorption and cell adherence are inhibited on the first surface, but not so inhibited on the second surface of said matrix; and placing the silk fibroin matrix at a site in need of such adhesion inhibition, such that the first surface inhibits adhesion of the treated tissues from opposing tissue surfaces or tissue-organ surface, and the second surface is contacted with the treated tissues to induce the cell and tissue ingrowth into the treated tissues.

The embodiments of the present invention also provide for methods of inhibiting thrombosis. For example, the method comprises providing a silk fibroin matrix having at least a first surface and a second surface, wherein the first surface has been modified by being coupled to PEG, such that blood protein adsorption and blood cell adherence is inhibited on the surface; and placing the silk fibroin matrix at a site in need of such thrombosis inhibition. More specifically, blood protein adsorption and blood cell adherence are inhibited on the first side but not so inhibited on the second side of said matrix. The silk fibroin matrix is placed at a site in need of such thrombosis inhibition, such that the first side is in contact with blood to prevent thrombosis, and said second side is in contact with surrounding tissues to induce the ingrowth of cells and tissues.

In the methods of using the surface modified or differentiated surface modified silk fibroin matrix for preventing or treating adhesion or thrombosis, the silk fibroin matrix may contain at least one active agent, such as one or more of the active agents discussed above. The strategies of loading active agents to silk matrices may be the same as discussed above. Embedding active agents in silk fibroin matrix may provide more therapeutic benefits to the silk fibroin-based materials. For example, the active agent may be embedded in the bulk of silk fibroin matrix or deposited onto the adherent side of silk fibroin matrix. Upon contacting the damaged tissues with the adherent side of the matrix, while the non-adherent side prevents tissue adhesions to the opposing tissues or organs, the active agents on the adherent side may be released to aid or inhibit certain functionalities of the damaged tissues. For example, the active agent may be cell growth factor to promote cell ingrowth and wound healing of the damaged tissues in contact, or anti-inflammatory agent to prevent post-surgical inflammatory disease.

In sum, silk fibroin is a biocompatible, mechanically robust, protein polymer available in several formats with controllable degradation rates. In the present invention, the amount of surface bound PEG was controlled and thereby resulted in PEGylated silk fibroin film surfaces with differences in wetting and other properties. Changes in concentration of the PEG grafted on silk fibroin surfaces permitted controlled adsorption of proteins and regulated proliferation of human fibroblasts, human mesenchymal stem cells, and human platelets. PEGylation could be restricted to one side of the film and therefore resulted in controlled adhesion of fibroblasts to one side of silk fibroin films. This "sided" approach to the biomaterial should is useful for advanced anti-adhesive biomaterial barriers and various anti-thrombotic applications.

EXAMPLES

Example 1

Formation of Silk Fibroin Films

Silk fibroin films were formed based on previously published protocols. See Karageorgiou et al., 71 J. Biomed. Mater. Res. A 528-37 (2004). Dry cocoons of *Bombyx mori* (Tajima Shoji Co, Yokohama, Japan) were boiled for 1 hr in a solution of 0.02 M $Na_2CO_3$ (Fisher Scientific, Pittsburgh, Pa.), to extract sericin from fibroin. Silk fibroin was washed thoroughly with distilled water to remove sericin, after which it was air dried. Removal of sericin was confirmed by weight ratio; dried silk mass to be 75% of the cocoon mass, ensuring removal of soluble sericin. The purified silk fibroin was dissolved in a 9.3 M LiBr solution at 50° C. to generate a 10% (w/v) solution. The solution was dialyzed in Slide-A-Lyzer cassettes with 3,500 MWCO (Pierce Chemicals, Rockford, Ill.) against water for three days to remove the LiBr. The solution was lyophilized and then dissolved in hexafluoro-2-propanol (HFIP) (Sigma-Aldrich, Milwaukee, Wis.) to generate a 2.5% silk solution. The 2.5% (w/v) silk solution was kept at 4° C. before making films.

Silk films were cast into either polystyrene weigh dishes (Fisher Scientific) or cell culture plates for different experiments. For 12- and 24-well cell culture plates, 225 µl and 118 µl of silk solution, respectively, was used to make films. To prepare free standing films, 2 ml of silk fibroin solution was added into a polystyrene weigh dish of 18.9 $cm^2$ area. All films were dried in a fume hood overnight. After evaporation of the hexafluoro-2-propanol overnight, methanol (Fisher Scientific) was added to the films for at least 30 min to induce the formation of β-sheets, securing insolubility of silk films in aqueous solutions. Films were stored covered at room temperature for use after evaporation of methanol. Conversion to β-sheet structure can result shrinking of free standing films. To avoid this outcome, PTFE boiling rocks (Norton, Derbyshire, UK) were used while methanol was evaporated. Films were hydrated in phosphate buffered saline, pH 7 (Invitrogen, Carlsbad, Calif.), before use.

Example 2

PEGylation of Silk Fibroin Films with Cyanuric Activated Poly(Ethylene Glycol)

The amount of activated PEG used in the reactions was determined by the surface area of silk fibroin for both free-standing films and films in cell culture plates. The volume of buffer used for solubilization of the cyanuric activated PEG, MW 5,000 (Sigma-Aldrich), was kept constant at 0.105 mL/$cm^2$ of silk fibroin. Cyanuric chloride is reactive to amine and hydroxyl groups. To increase the reactivity of the surface residues of silk fibroin film, the silk fibroin film was soaked in basic solution, e.g., 0.02 M $Na_3(BO)_3$ (pH 9), for a minimum of 30 min, before PEGylation. Different concentrations (0 mg/ml, 0.625 mg/ml, 1.25 mg/ml, 3.125 mg/ml, 6.25 mg/ml, 15.625 mg/ml, 31 mg/ml, and 62.5 mg/mL) of activated PEG were dissolved immediately in 0.02 M $Na_3(BO)_3$, pH 9, added to silk fibroin films and allowed to react overnight at 4° C.

Example 3

Determination of PEGylation on Silk Fibroin Films

An indirect analytical method was used to determine the amount of PEG grafted onto the silk fibroin films. An absorbance spectrum for cyanuric activated PEG (1.25 mg/mL) in borate buffer was developed. No absorbance was observed at visible wavelengths. The amount of PEG determined through absorbance at 240 nm was based on the triazine ring on cyanuric activated PEG. Boada et al., 253 Anal. Biochem. 33-36 (1997). A linear correlation between cyanuric activated PEG and absorbance at 240 nm was developed. The amount of PEG coupled on silk fibroin surface was determined as the difference in absorbance between activated solution applied to silk fibroin films and the absorbance of the solution removed from the silk films after reaction. The absorbance obtained from un-reacted PEG was compared with the standard curve developed.

Example 4

Differential PEGylation of Silk Film Surfaces

Free standing silk films were prepared as described in Example 2. Cyanuric chloride activated poly(ethylene glycol) was allowed to react to only one side of the film. Liquid was prevented from flowing to the film's underside by a "lip" on the top circumferential edge of the silk fibroin film that forms, naturally, during the film's development. PEG solution (62.5 mg/mL) solution was used for grafting PEG on one side of the film. The reaction proceeded at 4° C. overnight. Samples were carefully washed and then imaged to qualitatively demonstrate contact angle with Dulbecco's Modified Eagle Medium (Invitrogen).

Example 5

Contact Angle on PEGylated Silk Fibroin Films

Water contact angle was assessed using the sessile drop method. Two microliters (2 µL) of purified water (Milli-Q®, Millipore Corp., Billerica, Mass.) was spotted on PEGylated silk films and spreading was imaged using a goniometer (Rame-Hart, Inc., Mountain Lakes, NJ). Five to eight replicates on each group were tested. Finally, drop-spreading on various PEGylated silk fibroin films were compared with that on unmodified silk fibroin surfaces.

Example 6

Scanning Electron Microscopy (SEM) Analysis

Silk fibroin films covalently coupled with various amounts of activated PEG were analyzed by SEM. The unmodified silk fibroin films and silk films modified with PEG prepared from Examples 1 and 2 were sputter coated with gold for 10 sec under argon atmosphere and analyzed at an operating voltage of 15 kV.

Example 7

Protein Adsorption on PEGylated Films

Protein adsorption was measured on silk fibroin films covalently coupled with different amounts of activated PEG (silk fibroin films in 24-well plates reacted with 0 mg/mL, 0.625 mg/mL, 1.25 mg/mL, 3.125 mg/mL, 6.25 mg/mL, and 31 mg/mL activated PEG solution). Protein adsorption was determined using fluorescein isothiocyanate (FITC) labeled bovine serum albumin (BSA) and immunoglobulin G (IgG) (both purchased from Sigma). Aliquots of 250 µL of a 20 µg/mL solution of BSA and human IgG in phosphate buffered saline (PBS) (Invitrogen) were adsorbed on the silk films for 2 hr at 37° C. Subsequently, the wells were washed three times with 1 mL of PBS, and the fluorescence intensity of the surface was measured using a fluorescence microplate reader (Molecular Devices, Sunnyvale, Calif.). Excitation/Emission for FITC-labeled IgG and BSA were set at 490/520 nm.

Example 8

Isolation, Expansion and Culture of Human Mesenchymal Stem Cells (hMSCs)

A 25 mL aspirate of bone marrow from a male donor of less than 25-years-of-age (Cambrex, East Rutherford, N.J.) was plated in tissue culture flasks at a density of 200,000 cells/cm$^2$. Cells were isolated and expanded in a total of 35 mL of expansion media in 175 cm$^2$ flasks (Corning, Corning, N.Y.). hMSCs were separated from non-adhering hematopoietic cells as stromal cells adhered and expanded on tissue culture plastic. Expansion medium (17 mL) was added twice a week and adherent stromal cells were allowed to grow until 80% confluence (P0), after which they were trypsinized with 0.25% tryp sin (Invitrogen). All P0 cells were frozen and stored in 9% dimethylsulfoxide (DMSO) (Sigma-Aldrich), 91% fetal bovine serum (FBS) (Invitrogen). Expansion of passage 1 and passage 2 cells were initiated at a cell density of 5,000 cells/cm and then trypsinized at 80% confluency. Passage 2 cells were used to seed the silk fibroin films. Expansion media consisted of Dulbecco's Modified Eagle Medium (DMEM) (Invitrogen), 10% FBS, 1 ng/ml bFGF (Invitrogen), 0.1 mM non-essential amino acid (Invitrogen), 100 U/mL Penicillin-Streptomycin (Invitrogen) and 0.5 µg/ml fungizone (Invitrogen).

Trypsinized mesenchymal stem cells were counted via a hemocytometer. Silk fibroin-coated 12-well cell culture plates were seeded at a density of 5,000 cells/cm$^2$ in 2 mL of expansion medium. Cultures were allowed to expand on the silk film surfaces for 4 days. Cell proliferation was imaged and evaluated using a light microscope Zeiss Axiovert 5100 (Carl Zeiss, Jena, Germany) and Sony HAD 3CCD camera (Sony Corp., Tokyo, Japan) and relative cell counts were determined using alamar blue assays (Trek Diagnostic Systems, Cleveland, Ohio).

Example 9

Human Fibroblast Culture on Pegylated Silk Fibroin Films

Passage 11 to 13 of human lung fibroblasts (IMR-90) (American Type Culture Collection, Manassas, Va.) were used as a fibroblast cell type. Cells were expanded in Dulbecco's Modified Eagle Medium (DMEM) (Invitrogen), 20% FBS, 0.1 mM non-essential amino acids (Invitrogen) and 100 U/mL Penicillin-Streptomycin (Invitrogen) in T-25 flasks (Invitrogen). Cells were trypsinized when 80% confluent and seeded at 5,000 cells/cm$^2$ in 2 mL of expansion medium. Cells were cultured for various amount of time and imaged. Cell proliferation was evaluated via light microscopy, and cell counts were determined via alamar blue assay.

Example 10

Alamar Blue Assay

Alamar blue (Trek Diagnostic Systems), a non-toxic aqueous dye, was used to determine relative cell numbers, as known in the art. Relative cell numbers are indicated by measuring the reduction of resazurin to resorufin as indicator of metabolic state of cells. Medium was removed carefully from the cell cultures plates and replaced with 10% (v/v) alamar blue in expansion media. Alamar blue solution was incubated at 37° C. for 2.5 hr. Controls without cells were also incubated at 37° C. for 2.5 hr. A sample of 100 µL of reduced alamar blue solution was pipetted into costar opaque black bottom 96 plate wells (Sigma) and read at 560 (excitation)/590 (emission) in a spectrofluorometer micro titer well plate reader (Molecular Devices, Sunnyvale, Calif.). Fluorescence reading (590 nm) of media not exposed to cells but incubated for 2.5 hr was used as baseline measurement.

Example 11

Platelet Adhesion on PEGylated Silk Fibroin Films

Silk films prepared within 24-well plates were reacted with various concentrations of activated PEG. Platelet rich plasma (PRP) was purchased from Research Blood Components (Brighton, Mass., USA) and rocked at room temperature for a day. The platelet was gently centrifuged for 5 min at 1250 RPM to remove some red blood cells. Two ml (2 µL) of fresh platelets were directly plated on pre-wetted PEGylated silk fibroin films for 60 min at 37° C. The films were washed thrice with PBS. Adhered platelets were stained by Giemsa stain (Sigma-Aldrich) and observed with light microscopy. Adhered platelets were detected with giemsa stain. Two hundred microliters of undiluted giemsa stain was allowed to sit for 1.5 min on each of the PEGylated silk fibroin films. The stain was washed several times with PBS. Random images of all samples at 32× were taken from each of the three replicates. Platelets observed on the images were manually counted.

Statistical analysis: ANOVA was used for evaluating statistical differences between groups. Differences in groups with p value less than 0.05 were considered significant.

We claim:

1. A silk fibroin matrix comprising at least a portion of a first surface thereof selectively modified with poly(ethylene glycol) (PEG) at a density of about 75 µg PEG/cm$^2$ silk fibroin matrix to about 750 µg PEG/cm$^2$ silk fibroin matrix, so that the matrix is a PEGylated matrix,
    wherein the PEG is not substantially present in the bulk of the silk fibroin matrix, and does not alter bulk material properties of the silk fibroin matrix in that the PEGylated matrix shows one or more bulk material properties that are substantially identical or equivalent to those displayed by an otherwise identical silk fibroin matrix lacking the PEG.

2. The silk fibroin matrix of claim 1, wherein the PEGylated matrix is degraded at a reduced rate relative to degradation observed with an otherwise identical matrix lacking the PEG.

3. The silk fibroin matrix of claim 1, wherein the PEGylated matrix inhibits or prevents adherence of tissues to opposing tissues or organs.

4. The silk fibroin matrix of claim 1, wherein the PEGylated matrix shows one or both of:
    reduced adsorption of proteins of about 150 kDa or larger, increased adsorption of proteins of about 70 kDa or smaller, relative to adsorption observed with an otherwise identical matrix lacking the PEG.

5. The silk fibroin matrix of claim 1, wherein at least a portion of a second surface of the silk fibroin matrix is modified with PEG at a density different from or the same as that of the density of the PEG on at least a portion of a first surface, so that the matrix is a PEGylated matrix.

6. The silk fibroin matrix of claim 1, wherein the PEG density is at least about 187.5 µg PEG/cm$^2$ silk fibroin matrix.

7. The silk fibroin matrix of claim 1, further comprising at least one active agent.

8. The silk fibroin matrix of claim 7, wherein the at least one active agent is selected from the group consisting of cells, proteins, peptides, nucleic acid analogues, nucleotides or oligonucleotides, peptide nucleic acids, aptamers, antibodies or fragments or portions thereof, hormones, hormone antagonists, growth factors or recombinant growth factors and fragments and variants thereof, cytokines, enzymes, antibiotics or antimicrobial compounds, viruses, antivirals, toxins, prodrugs, chemotherapeutic agents, small molecules, drugs, and any combinations thereof.

9. The silk fibroin matrix of claim 1, wherein the silk fibroin matrix is a biomaterial for placement in a subject.

10. The silk fibroin matrix of claim 9, wherein the placement of said silk fibroin matrix in said subject is at a site of potential tissue adhesion or thrombosis.

11. The silk fibroin matrix of claim 1, wherein the silk fibroin matrix is a coating on a medical device or an implant.

12. A method for producing a silk fibroin matrix having at least a portion of a first surface modified with poly(ethylene glycol) (PEG), at a density of about 75 µg PEG/cm$^2$ silk fibroin matrix to about 750 µg PEG/cm$^2$ silk fibroin matrix, so that the matrix is a PEGylated matrix,
wherein the PEG is not substantially present in the bulk of the silk fibroin matrix and does not alter bulk material properties of the silk fibroin matrix, in that the PEGylated matrix shows one or more bulk material properties that are substantially identical or equivalent to those displayed by an otherwise identical silk fibroin matrix lacking the PEG, comprising:
providing a silk fibroin matrix, wherein the silk fibroin matrix is solid-state, and optionally hydrating the silk fibroin matrix; and
reacting said at least a portion of the first surface of the silk fibroin matrix with a functional group-activated PEG for a time sufficient for the functional group-activated PEG to bind to said at least a portion of the first surface of the silk fibroin matrix.

13. The method of claim 12, further comprising activating said at least a portion of the first surface of the silk fibroin matrix in a basic aqueous solution.

14. The method of claim 12, wherein the reaction of binding the functional group-activated PEG to said at least a portion of the first surface of the silk fibroin matrix is through cyanuric chloride-activated coupling reaction, wherein the functional group-activated PEG is a cyanuric chloride-activated PEG.

15. The method of claim 12, wherein the reaction of binding the functional group-activated PEG to said at least a portion of the first surface of the silk fibroin matrix is through diazonium coupling reaction, wherein the functional group-activated PEG is PEG substituted diazonium salt.

16. The method of claim 12, wherein the reaction of binding the functional group-activated PEG to said at least a portion of the first surface of the silk fibroin matrix is through carbodiimide coupling reaction.

17. The method of claim 12, further comprising reacting at least a portion of a second surface of the silk fibroin matrix with a functional group-activated PEG for a time sufficient for said functional group-activated PEG to bind to said at least a portion of the second surface of the silk fibroin matrix.

18. The silk fibroin matrix of claim 2, wherein the degradation is proteolytic degradation.

19. The silk fibroin matrix of claim 2, wherein the portion of a first surface of the PEGylated matrix is degraded at a reduced rate relative to a second surface lacking the PEG.

20. The silk fibroin matrix of claim 3, wherein the tissues or organs are normally separated.

21. The silk fibroin matrix of claim 1, wherein the PEGylated matrix shows decreased attachment and proliferation of a cell relative to attachment of a cell observed with an otherwise identical matrix lacking the PEG.

22. The silk fibroin matrix of claim 21, wherein the cell is a fibroblast or a mesenchymal stem cell.

23. The silk fibroin matrix of claim 1, wherein the PEGylated matrix shows decreased attachment of platelets relative to attachment of platelets observed with an otherwise identical matrix lacking the PEG.

24. The silk fibroin matrix of claim 4, wherein the protein of about 150 kDa or larger is an antibody and the protein of about 70 kDa or smaller is a blood protein.

25. The silk fibroin matrix of claim 9, wherein the biomaterial is an adhesion barrier material or a thrombotic barrier material.

26. The silk fibroin matrix of claim 10, wherein the site of potential tissue adhesion is or comprises a site between tissues that are normally separated.

27. The silk fibroin matrix of claim 10, wherein the site of potential thrombosis is a site where the first surface is in contact with blood.

28. The silk fibroin matrix of claim 27, wherein the second surface lacks PEG and is in contact with surrounding tissues such that ingrowth of cells and tissues is induced.

* * * * *